(12) United States Patent
Dinsmoor et al.

(10) Patent No.: US 11,439,825 B2
(45) Date of Patent: Sep. 13, 2022

(54) DETERMINING POSTURE STATE FROM ECAPS

(71) Applicant: Medtronic, Inc., Minneapolis, MN (US)

(72) Inventors: David A. Dinsmoor, North Oaks, MN (US); Christopher L. Pulliam, Plymouth, MN (US); Kristin N. Hageman, Dayton, MN (US); Hank Bink, Minneapolis, MN (US); Jiashu Li, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 340 days.

(21) Appl. No.: 16/721,576

(22) Filed: Dec. 19, 2019

(65) Prior Publication Data
US 2021/0187300 A1    Jun. 24, 2021

(51) Int. Cl.
*A61N 1/36* (2006.01)
*A61B 5/389* (2021.01)
*A61B 5/11* (2006.01)

(52) U.S. Cl.
CPC ........ *A61N 1/36139* (2013.01); *A61B 5/1116* (2013.01); *A61B 5/389* (2021.01); *A61N 1/36192* (2013.01); *A61B 2562/0219* (2013.01)

(58) Field of Classification Search
None
See application file for complete search history.

(56) References Cited

U.S. PATENT DOCUMENTS

| | | |
|---|---|---|
| 8,515,549 B2 | 8/2013 | Panken et al. |
| 8,918,177 B2 | 12/2014 | Gauthier |
| 8,958,885 B2 | 2/2015 | Panken et al. |
| 9,084,900 B2 | 7/2015 | Hershey et al. |
| 9,302,112 B2 | 4/2016 | Bornzin et al. |
| 9,381,356 B2 | 7/2016 | Parker et al. |
| 9,511,231 B1 | 12/2016 | Kent et al. |
| 9,553,148 B2 | 1/2017 | Carcieri |
| 10,327,654 B2 | 6/2019 | Strahl et al. |

(Continued)

FOREIGN PATENT DOCUMENTS

| | | |
|---|---|---|
| CN | 105792745 A | 7/2016 |
| EP | 3024540 B1 | 6/2016 |

(Continued)

OTHER PUBLICATIONS

International Search Report and Written Opinion of International Application No. PCT/US2020/060331, dated Feb. 15, 2021, 10 pp.

(Continued)

*Primary Examiner* — Ankit D Tejani

(74) *Attorney, Agent, or Firm* — Shumaker & Sieffert, P.A.

(57) ABSTRACT

Systems, devices, and techniques are described for determining a posture state of a patient based on detected evoked compound action potentials (ECAPs). In one example, a medical device includes stimulation circuitry configured to deliver electrical stimulation and sensing circuitry configured to sense a plurality of evoked compound action potential (ECAP) signals. The medical device also includes processing circuitry configured to control the stimulation circuitry to deliver a plurality of electrical stimulation pulses having different amplitude values, control the sensing circuitry to detect, after delivery of each electrical stimulation pulse of the plurality of electrical stimulation pulses, a respective ECAP signal of the plurality of ECAP signals, and determine, based on the plurality of ECAP signals, a posture state of the patient.

26 Claims, 8 Drawing Sheets

(56) References Cited

U.S. PATENT DOCUMENTS

| | | |
|---|---|---|
| 2014/0236257 A1 | 8/2014 | Parker et al. |
| 2014/0277282 A1 | 9/2014 | Jaax |
| 2015/0032181 A1 | 1/2015 | Baynham et al. |
| 2015/0173636 A1 | 6/2015 | Mokelke et al. |
| 2015/0360031 A1 | 12/2015 | Bornzin et al. |
| 2016/0157769 A1 | 6/2016 | Min et al. |
| 2016/0287126 A1 | 10/2016 | Parker et al. |
| 2016/0339251 A1 | 11/2016 | Kent et al. |
| 2017/0135624 A1 | 5/2017 | Parker |
| 2017/0361101 A1 | 12/2017 | Single |
| 2018/0110987 A1 | 4/2018 | Parker |
| 2018/0126169 A1 | 5/2018 | Hou et al. |
| 2019/0168000 A1 | 6/2019 | Laird-Wah |
| 2019/0209844 A1* | 7/2019 | Esteller .............. A61N 1/36132 |
| 2020/0046980 A1* | 2/2020 | Moffitt ............... A61N 1/36192 |

FOREIGN PATENT DOCUMENTS

| | | |
|---|---|---|
| JP | 2018513714 A | 5/2018 |
| WO | 2012155188 A1 | 11/2012 |
| WO | 2015070281 A1 | 5/2015 |
| WO | 2016011512 A1 | 1/2016 |
| WO | 2016090436 A1 | 6/2016 |
| WO | 2017100866 A1 | 6/2017 |
| WO | 2017173493 A1 | 10/2017 |
| WO | 2017219096 A1 | 12/2017 |
| WO | 2019204884 A1 | 10/2019 |

OTHER PUBLICATIONS

Laird-Wah, "Improving Spinal Cord Stimulation—Model-Based Approaches to Evoked Response Telemetry," Dissertation submitted to the University of South Wales, Aug. 2015, 273 pp.

Shariati et al., "Evaluating Spinal Cord Stimulation incorporating feedback control using Evoked Compound Action Potential," Saluda Medical, Dec. 2, 2014, 1 pp.

U.S. Appl. No. 16/721,491, by Medtronic, Inc. (Inventors: Dinsmoor et al.), filed Dec. 19, 2019.

U.S. Appl. No. 16/721,528 by Medtronic, Inc. (Inventors: Dinsmoor et al.), filed Dec. 19, 2019.

* cited by examiner

DETERMINING POSTURE STATE FROM ECAPS

TECHNICAL FIELD

This disclosure generally relates to electrical stimulation, and more specifically, determining characteristics of a patient using electrical stimulation.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers.

SUMMARY

In general, systems, devices, and techniques are described for determining a posture state of a patient based on one or more evoked compound action potential (ECAPs) signals sensed from a patient. When a patient moves, the distance between implanted electrodes and target nerves changes. For example, electrodes implanted along the spinal column are closer to the spinal cord when a subject lies in a supine posture state as compared to a standing posture state. Similarly, the implanted electrodes may move closer to the spinal cord when a subject coughs or sneezes. Therefore, a characteristic of the ECAP signal changes according to the stimulation pulse that evoked the ECAP signal and the distance between the electrodes and the nerves.

Devices and systems described herein may leverage the relationship between stimulation pulse parameters and the characteristic of the ECAP signal to determine the posture state currently occupied by the subject. For example, an implantable medical device (IMD) may deliver a plurality of stimulation pulses with different stimulation parameter values and detect the resulting ECAP signals from each pulse. The IMD may then determine the relationship between the stimulation parameter values and one or more characteristics of the resulting ECAP signals and identify the posture state of the subject. In some examples, the IMD may transmit the identified posture state to an external device for display to a user. In some examples, the IMD may use the identified posture state as feedback to control therapy delivery to the subject. For example, the IMD may select stimulation parameter values for electrical stimulation based on the identified posture state or select a target ECAP value for the identified posture state for modulating stimulation parameter values.

In one example, a system includes stimulation circuitry configured to deliver electrical stimulation, sensing circuitry configured to sense a plurality of evoked compound action potential (ECAP) signals, and processing circuitry configured to control the stimulation circuitry to deliver a plurality of electrical stimulation pulses having different amplitude values, control the sensing circuitry to detect, after delivery of each electrical stimulation pulse of the plurality of electrical stimulation pulses, a respective ECAP signal of the plurality of ECAP signals, and determine, based on the plurality of ECAP signals, a posture state of the patient.

In another example, a method includes controlling, by processing circuitry, stimulation circuitry to deliver a plurality of electrical stimulation pulses having different amplitude values, controlling, by the processing circuitry, sensing circuitry to detect, after delivery of each electrical stimulation pulse of the plurality of electrical stimulation pulses, a respective evoked compound action potential (ECAP) signal of a plurality of ECAP signals, and determining, by the processing circuitry and based on the plurality of ECAP signals, a posture state of the patient.

In another example, a computer-readable medium includes instructions that, when executed, causes processing circuitry to control stimulation circuitry to deliver a plurality of electrical stimulation pulses having different amplitude values, control sensing circuitry to detect, after delivery of each electrical stimulation pulse of the plurality of electrical stimulation pulses, a respective evoked compound action potential (ECAP) signal of a plurality of ECAP signals, and determine, based on the plurality of ECAP signals, a posture state of the patient.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
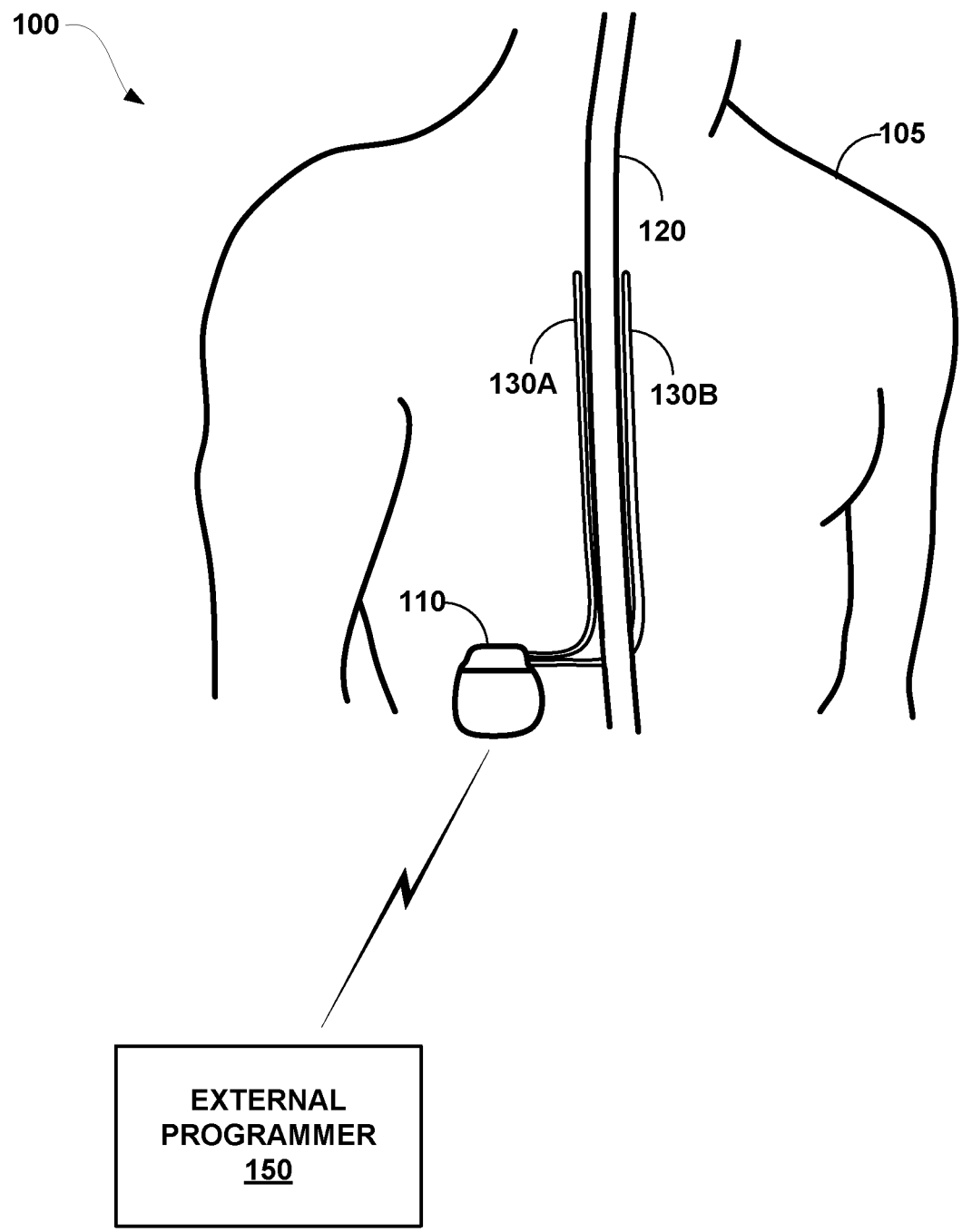
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for determining a posture state of a subject based on one or more characteristics of evoked compound action potentials (ECAPs). Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. However, as the patient moves, the distance between the electrodes and the target tissues changes. Since neural recruitment at the nerves is a function of stimulation intensity (e.g., amplitude and/or pulse frequency) and distance between the target tissue and the electrodes, movement of the electrode closer to the target tissue may result in increased neural recruitment (e.g., possible painful sensations or adverse motor function), and movement of the electrode further from the target tissue may result in decreased efficacy of the therapy for the patient. Certain patient postures (which may or may not include patient activity) may be representative of respective distances (or changes in distance) between electrodes and nerves and thus be an informative feedback variable for modulating stimulation therapy.

ECAPs are a measure of neural recruitment because each ECAP signal represents the superposition of electrical potentials generated from a population of axons firing in response to an electrical stimulus (e.g., a stimulation pulse). Changes in a characteristic (e.g., an amplitude of a portion of the signal or area under the curve of the signal) of an ECAP signals occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude). Therefore, a system can determine that the distance between electrodes and nerves has increased or decreased in response to determining that the measured ECAP characteristic value has increased or decreased. For example, if the set of parameter values stays the same and the ECAP characteristic value of amplitude increases, the system can determine that the distance between electrodes and the nerve has decreased.

In some examples, effective stimulation therapy may rely on a certain level of neural recruitment at a target nerve. This effective stimulation therapy may provide relief from one or more conditions (e.g., patient perceived pain) without an unacceptable level of side effects (e.g., overwhelming perception of stimulation). However, if the patient changes posture or otherwise engages in physical activity, the distance between the electrodes and the nerve changes as well. This change in distance can cause loss of effective therapy and/or side effects if the parameter values that define stimulation pulses are not adjusted to compensate for the change in distance. A system may change stimulation parameters to compensate for changes to the distance between electrodes and the target nerve, such as increasing stimulation intensity in response the distance increases and decreasing stimulation intensity in response to the distance decreasing. However, the magnitude of any changes to stimulation parameter values may be influenced by what posture state the patient moved to. Therefore, the system may perform more accurate changes to stimulation parameter values if the actual posture state of the patient is known and the parameter values selected to correspond to that posture state.

As described herein, systems, devices, and techniques are described for determining a posture state of a patient based on one or more evoked compound action potential (ECAPs) signals sensed from a patient. As discussed above, when a patient moves, the distance between implanted electrodes and target nerves changes. For example, electrodes implanted along the spinal column move to a position closer to the spinal cord when a subject lies in a supine posture state as compared to a position farther from the spinal cord when the subject assumes a standing posture state. Similarly, the implanted electrodes may move closer to the spinal cord during a transient event such as when a subject coughs, laughs, or sneezes. Therefore, a characteristic value of the ECAP signal changes according to the stimulation pulse that evoked the ECAP signal and the distance between the electrodes and the nerves.

A system may leverage the relationship between stimulation pulse parameters and the characteristic of the ECAP signal to determine the posture state currently occupied by the subject. For example, an implantable medical device (IMD) may deliver a plurality of stimulation pulses with different stimulation parameter values and detect the resulting ECAP signals from each respective pulse. Based on the detected ECAP signals, the IMD may determine a relationship between the stimulation parameter values and one or more characteristics of the resulting ECAP signals to identify the posture state of the subject. In one example, the relationship may be the amplitude values of the ECAP signals with respect to the amplitude of the respective pulses that evoked each ECAP signal. A steeper curve between these values may represent a posture state (e.g., the supine position) that has a closer distance between electrodes and the target nerve than a shallower curve between the values of a posture state (e.g., the prone position) having a further distance between electrodes and the target curve.

In some examples, the IMD may employ the identified posture state as feedback to control therapy delivery to the subject. For example, the IMD may select stimulation parameter values for electrical stimulation based on the identified posture state or select a target ECAP value for the identified posture state for modulating stimulation parameter values. In some examples, the IMD may select a growth curve that corresponds to the identified posture state and adjust stimulation parameter values for subsequent stimulation pulses according to the selected growth curve. In addition, or alternatively, the IMD may transmit the identified posture state to an external device for display to a user (e.g., via an external programmer). In some examples, the IMD or other device may store the identified posture state and/or perform patient monitoring activities using identified posture states detected over time.

In some examples, the ECAPs detected by an IMD may be ECAPs elicited by stimulation pulses intended to contribute to therapy of a patient or separate pulses configured to elicit ECAPs that are detectable by the IMD. Nerve impulses detectable as the ECAP signal travel quickly along the nerve fiber after the delivered stimulation pulse first depolarizes the nerve. If the stimulation pulse delivered by first electrodes has a pulse width that is too long, different electrodes configured to sense the ECAP will sense the stimulation pulse itself as an artifact that obscures the lower amplitude ECAP signal. However, the ECAP signal loses fidelity as the electrical potentials propagate from the electrical stimulus because different nerve fibers propagate electrical potentials at different speeds. Therefore, sensing the ECAP at a far distance from the stimulating electrodes may avoid the artifact caused by a stimulation pulse with a long pulse width, but the ECAP signal may lose fidelity needed to detect changes to the ECAP signal that occur when the electrode to target tissue distance changes. In other words, the system may not be able to identify, at any distance from the stimulation electrodes, ECAPs from stimulation pulses configured to provide a therapy to the patient.

In some examples, ECAPs are detectable from pulses intended to contribute to the therapy of a patient. However, when these therapy pulses cause artifacts that interfere with the IMD's ability to detect the ECAP, the IMD may be configured to deliver pulses separate from pulses intended to contribute to therapy for the purpose of detecting ECAPs without interference from the pulses themselves. The pulses configured to elicit detectable ECAPs may be referred to as control pulses, and the pulses from which ECAPs are not detectable, but otherwise are adjusted according to the ECAP signals, may be referred to as informed pulses. In this manner, the plurality of control pulses may or may not contribute to therapy received by the patient, and the informed pulses may generally be configured to contribute to therapy received by the patient. Therefore, the IMD or other component associated with the medical device may determine values of one or more stimulation parameters that at least partially define the informed pulses based on an ECAP signal elicited by a control pulse instead. For example, the control pulses may be configured to elicit ECAPs used to detect the posture state of the patient. In this manner, the informed pulse may be informed by the ECAP elicited from a control pulse. The medical device or other component associated with the medical device may determine values of one or more stimulation parameters that at least partially define the control pulses based on an ECAP signal elicited by previous control pulse.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In some examples, the stimulation signals, or pulses, may be configured to elicit detectable ECAP signals that IMD 110 may use to determine the posture state occupied by patient 105 and/or determine how to adjust one or more parameters that define stimulation therapy. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

If control pulses separate from the informed pulses used for therapy are needed to elicit a detectable ECAP signal, system 100 may employ an ECAP test stimulation program that defines stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses. However, the stimulation defined by each ECAP test stimulation program are not intended to provide or contribute to therapy for the patient. In addition, the ECAP test stimulation program may define the control pulses used for each sweep of pulses that are used to determine the posture state of the patient.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IM 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IM 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

Furthermore, IMD 110 may be configured to deliver control stimulation to patient 105 via a combination of electrodes of leads 130, alone or in combination with an electrode carried by or defined by an outer housing of IMD 110 in order to detect ECAP signals (e.g., control pulses and/or informed pulses). The tissue targeted by the stimulation may be the same or similar tissue targeted by the electrical stimulation therapy, but IMD 110 may deliver stimulation pulses for ECAP signal detection via the same, at least some of the same, or different electrodes. Since control stimulation pulses can be delivered in an interleaved manner with informed pulses (e.g., when the pulses configured to contribute to therapy interfere with the detection of ECAP signals or pulse sweeps intended for posture state detection via ECAP signals do not correspond to pulses intended for therapy purposes), a clinician and/or user may select any desired electrode combination for informed pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 can deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105. In some examples, the ECAP test stimulation program may also define the number of pules and parameter values for each pulse of multiple pulses within a pulse sweep configured to obtain a plurality of ECAP signals for respective pulses in order to obtain the growth curve that IMD 110 may use to determine the current posture state of the patient. In some examples, IMD 110 delivers control stimulation to patient 105 according to multiple ECAP test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as electrical stimulation therapy (e.g., informed pulses) and/or control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

As described herein, IMD 110 may be configured to detect ECAP signals which are representative of the number of nerve fibers activated by a delivered stimulation signal (e.g., a delivered pulse). Since the distance between both the stimulating and sensing electrodes and the target nerve changes for different posture states (e.g., a static posture and/or activity component), a characteristic value of one or more ECAP signals can be indicative of the posture state currently occupied when the one or more ECAP signals were detected by IMD 110. In one example, IMD 110 may deliver a plurality of pulses defined by different parameter values and detect the respective ECAP signal elicited by each pulse. IM 110 may determine a relationship between characteristic values from each ECAP signal and the different parameter values of the pulses, and this relationship may be different for each different posture state. In one example, the relationship may be a curve of the characteristic values of the ECAP (e.g., an amplitude of the ECAP signal) vs. values of a stimulation parameter (e.g., the current amplitude of the respective pulses) that elicited each ECAP signal from which the characteristic values were derived. Each posture state may have a respective curve that varies in slope and/or intercept. In this manner, IMD 110 may determine the posture state by comparing the determined relationship to previously stored relationships for each posture state of a plurality of different posture states.

In some examples, IMD 110 may detect ECAP signals from pulses delivered for the purpose of providing therapy to the patient. In other examples, the pulses configured to provide therapy to the patient may interfere with the detection of the ECAP signals. In this manner, the therapy pulses may be referred to as informed pulses because the parameter values that define the informed pulses may be determined by IMD 110 according to ECAP signals elicited from different control pulses.

In one example, each informed pulse may have a pulse width greater than approximately 300 □s, such as between approximately 300 □s and 1000 □s (i.e., 1 millisecond) in some examples. At these pulse widths, IMD 110 may not sufficiently detect an ECAP signal because the informed pulse is also detected as an artifact that obscures the ECAP signal. When pulses intended to provide therapy have these longer pulse widths, IMD 110 may deliver control stimulation in the form of control pulses in order to detect ECAP signals. The control pulses may have pulse widths of less than the interfering therapy pulses (e.g., less than approximately 300 □s), such as a bi-phasic pulse with each phase having a duration of approximately 100 □□s. Since the control pulses may have shorter pulse widths than the informed pulses, the ECAP signal may be sensed and identified following each control pulse and used to inform IMD 110 about any changes that should be made to the informed pulses (and control pulses in some examples). In general, the term "pulse width" refers to the collective duration of every phase, and interphase interval when appropriate, of a single pulse. A single pulse includes a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 □s, a negative phase lasting 100 □s, and an interphase interval lasting 30 □s defines a pulse width of 230 □s). In other examples, a biphasic pulse may have a positive phase lasting 120 □s, a negative phase lasting 120 □s, and an interphase interval lasting 30 □s defines a pulse width of 270 □s.

In this disclosure, efficacy of electrical stimulation therapy may be indicated by one or more characteristics (e.g. an amplitude of or between one or more peaks or an area under the curve of one or more peaks) of an action potential that is evoked by a stimulation pulse delivered by IMD 110 (i.e., a characteristic value of the ECAP signal). Electrical stimulation therapy delivery by leads 130 of IMD 110 may cause neurons within the target tissue to evoke a compound action potential that travels up and down the target tissue, eventually arriving at sensing electrodes of IMD 110. Furthermore, stimulation (e.g., therapy pulses and/or control pulses) may also elicit at least one ECAP signal, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

Example techniques for adjusting stimulation parameter values for informed pulses (e.g., pulses configured to contribute to therapy for the patient) are based on comparing the value of a characteristic of a measured ECAP signal to a target ECAP characteristic value. During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of patient 105. Examples of the one or more sensors include one or more sensors configured to measure a compound action potential of patient 105, or a physiological effect indicative of a compound action potential. For example, to measure a physiological effect of a compound action potential, the one or more sensors may be an accelerometer, a pressure sensor, a bending sensor, a sensor configured to detect a posture of patient 105, or a sensor configured to detect a respiratory function of patient 105. However, in other examples, external programmer 150 receives a signal indicating a compound action potential in the target tissue of patient 105 and transmits a notification to IMD 110.

In the example of FIG. 1, IMD 110 described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more stimulation parameter that defines the electrical stimulation informed pulses and, in some examples, control pulses, delivered to patient 105.

In the example techniques described in this disclosure, the control stimulation parameters and the target ECAP characteristic values may be initially set at the clinic but may be set and/or adjusted at home by patient 105. For example, the target ECAP characteristics may be changed to match or be a fraction of a stimulation threshold. In some examples, target ECAP characteristics and/or growth curves may be specific to respective different posture states of the patient.

And, as discussed herein, the patient's posture state may be determined based on one or more characteristic values of ECAP signals detected for the patient. Once the target ECAP characteristic values are set, the example techniques allow for automatic adjustment of informed pulse parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 105.

In some examples, the system changes the target ECAP characteristic value and/or growth rate(s) over a period of time, such as according to a change to a stimulation threshold (e.g., a perception threshold or detection threshold). The system may be programmed to change the target ECAP characteristic in order to adjust the intensity of informed pulses to provide varying sensations to the patient (e.g., increase or decrease the volume of neural activation). Although the system may change the target ECAP characteristic value, received ECAP signals may still be used by the system to adjust one or more parameter values of the informed pulses and/or control pulses in order to meet the target ECAP characteristic value.

One or more devices within system 100, such as IMD 110 and/or external programmer 150, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses having different amplitude values and control the sensing circuitry to detect, after delivery of each electrical stimulation pulse of the plurality of electrical stimulation pulses, a respective ECAP signal of the plurality of ECAP signals. The processing circuitry of IMD 110 may then determine, based on the plurality of ECAP signals, a posture state of the patient.

In some examples, IMD 110 may include the stimulation circuitry, the sensing circuitry, and the processing circuitry. However, in other examples, one or more additional devices may be part of the system that performs the functions described herein. For example, IMD 110 may include the stimulation circuitry and the sensing circuitry, but external programmer 150 or other external device may include the processing circuitry that at least determines the posture state of the patient. IMD 110 may transmit the sensed ECAP signals, or data representing the ECAP signal, to external programmer 150, for example. Therefore, the processes described herein may be performed by multiple devices in a distributed system. In some examples, system 100 may include one or more electrodes that deliver and/or sense electrical signals. Such electrodes may be configured to sense the ECAP signals. In some examples, the same electrodes may be configured to sense signals representative of transient movements of the patient. In other examples, other sensors, such as accelerometers, gyroscopes, or other movement sensors may be configured to sense movement of the patient that indicates the patient may have transitioned to a different posture state. In this manner, IMD 110 may redetect the posture state of the patient from new ECAP signals.

The posture state of the patient may be a static posture of the patient and/or an activity level of the patient. For example, the static posture may be a prone position, supine position, left lateral recumbency (lying left side position), right lateral recumbency (lying right side position), reclining position, sitting position, or standing position. Each of these positions may be a separate posture state. The posture state may also, or alternatively, be an activity level of the patient. For example, the posture state may include activities such as walking, running, bicycle riding, driving in a car, etc. In some examples, the posture state may represent a static posture and an activity. These combinations of posture and activity may represent situations where the patient is in a static posture while moving, such as being in a vehicle that is moving. Any of these posture states may be included in a plurality of posture states from which IMD 110 may determine the current posture state of the patient. This this manner, the processing circuitry of IMD 110 may be configured to determine the posture state by selecting the posture state from a plurality of posture states, where the plurality of posture states may include at least two of a prone position, a supine position, a sitting position, and a standing position.

As discussed herein, the determined posture state may be stored in memory, transmitted to another device, and/or presented to a user via a user interface. In this manner, a log of patient movement may be constructed over time. In some examples, IMD 110 may determine a therapy is effective by detecting greater movement by the patient that may indicate pain is no longer restricting patient movement. In some examples, IMD 110 may be configured to adjust, based on the determined posture state, a value of one or more parameters that at least partially define electrical stimulation therapy for the patient. For example, IMD 110 may select specific parameter values for the detected posture state, select a target ECAP characteristic value for the detected posture state, and/or select a growth curve for the detected posture state for use in increasing or decreasing stimulation parameters intended to maintain volume of activation of nerve fibers (e.g., maintain consistent therapy levels).

As discussed above, IMD 110 may deliver a plurality of electrical stimulation pulses having different amplitude values in order to elicit respective ECAP signals having different characteristic values representing the ECAP signals. In general, the different amplitude values are lower than a discomfort threshold for the patient. However, in some examples, one or more pulses may have an amplitude that exceeds the discomfort threshold for the patient. In some examples, the different amplitudes may be current or voltage amplitudes of the pulses. The amplitudes may be selected to have as low values as possible in order to reduce any perceived stimulus by the patient. The discomfort threshold may be determined by a clinician during initial implantation, but the clinician or patient may update the discomfort threshold over time. IMD 110 may select the amplitudes of the delivered pulses to be less than the discomfort threshold or less than some percentage of the discomfort threshold (e.g., less than some safety factor less than the discomfort threshold).

In some examples, the processing circuitry of IMD 110 may be configured to determine characteristic values for the plurality of ECAP signals detected after each of the plurality of electrical stimulation pulses. The characteristic value for each ECAP signal is a representation of the ECAP signal according to some metric. For example, the characteristic value may be the amplitude between the N1 and P2 toughs/peaks in the ECAP signal or the area under the curve of a trough/peak (e.g., the P2 peak) of the ECAP signal. These characteristic values may thus be used as a metric derived from the ECAP signal the represents the relative nerve fiber activation caused by the delivered stimulation pulse. In this manner, each ECAP signal of the plurality of ECAP signals will be associated with a respective characteristic value of the characteristic values. As long as the distance between the electrodes and target nerve remains relatively constant during delivery of the pulses and sensing of the respective ECAP signals, higher amplitude pulses generally cause more neural recruitment and larger ECAP signals.

Figure 6:
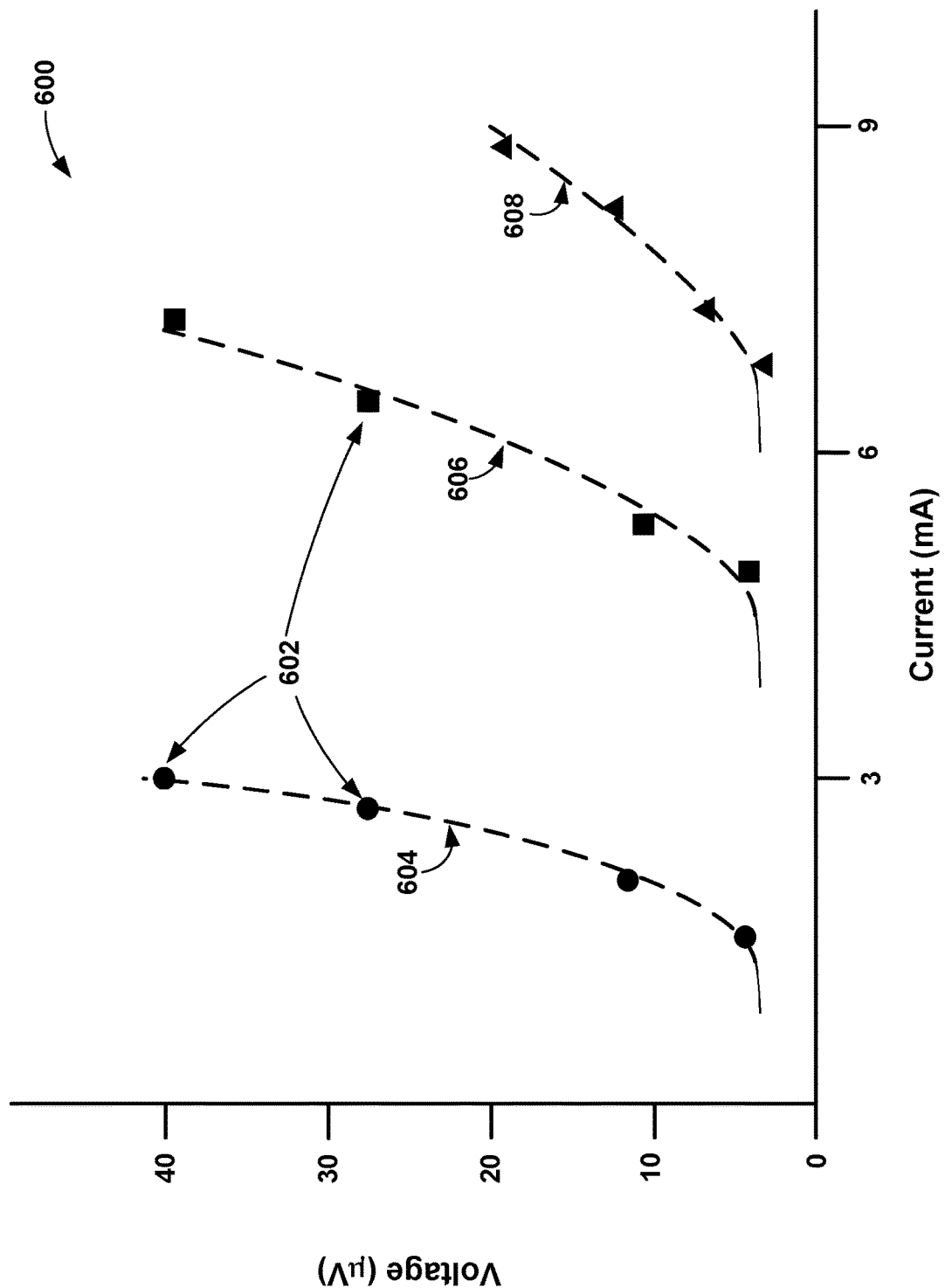
FIG. 6 is a graph illustrating example growth curves for a relationship between ECAP amplitude and pulse amplitude for different posture states.

IMD 110 may then determine a growth curve representing a relationship between the characteristic values of the plurality of ECAP signals and the different amplitude values of the plurality of electrical stimulation pulses from which the ECAP signals were evoked. This growth curve may be generally linear when comparing the voltage amplitude of the ECAP signals to the current amplitudes from each respective stimulation pulse (e.g., as shown in FIG. 6 below). IMD 110 may then compare the determined growth curve to a plurality of calibration growth curves associated with respective posture states of a plurality of posture states. These calibration growth curves may be growth curves previously associated with respective posture states (i.e., known growth curves expected for each posture state). IMD 110 may then determine, based on the comparison, the posture state of the patient. For example, IMD 110 may select the posture state that has the calibration growth curve closest to the determined growth curve.

The delivery of the electrical stimulation pulses having different amplitude values may be referred to as a sweep of pulses. For example, IMD 110 may be configured to control the stimulation circuitry to deliver the plurality of electrical stimulation pulses as a sweep of pulses comprising iteratively increasing amplitude values. However, the pulses may have decreasing amplitude values or randomly selected amplitude values in other examples. IMD 110 may detect the ECAP signal from the previous stimulation pulse prior to delivering the next stimulation pulse. Therefore, IMD 110 may schedule a detection window of time between the delivery of each pulse within the sweep of pulses.

In some examples, IMD 110 may start the sweep of pulses over again if movement of the patient is detected. IMD may thus control, during a first period of time, the stimulation circuitry to deliver a first set of electrical stimulation pulses from which respective ECAP signals of a first set of ECAP signals can be detected. However, IMD 110 may be configured to identify, during the first period of time, a transient movement of the patient. Such a transient movement may be a cough, sneeze, laugh, or bending motion of the patient that would likely cause the distance between the electrodes and target tissue to change. Responsive to identifying the transient movement, IMD 110 may terminate the first period of time and the delivery of the first set of electrical stimulation pulses and discard the first set of ECAP signals. The first set of ECAP signals may not be valuable because the posture state of the patient has likely changed. IMD 110 may monitor the transient movement and then determine that the transient movement has ended. For example, IMD 110 may determine that more movement has not been detected for a predetermined period of time. Then, after the transient movement has ended, IMD 110 may be configured to control the stimulation circuitry to deliver the second set of electrical stimulation pulses and control the sensing circuitry to detect the second set of ECAP signals. This process can continue until a full sweep is completed. In this manner, IMD 110 can restart the sweep of pulses in response to determining that the transient movement has ended in an attempt to determine the new posture state of the patient from ECAP signals.

In some examples, IMD 110 may detect the transient movement from the ECAP signals themselves during the sweep. For example, IMD 110 may determine that the ECAP characteristic value is not within an acceptable deviation from a linear increase with increasing pulse intensity. Since the overall growth curve for a posture state may typically be linear, IMD 110 may analyze determined characteristic values from subsequent ECAP signals during the sweep to determine if the characteristic values start to deviate from the expected linear growth curve by a predetermined deviation (e.g., a magnitude or a percentage). If IMD 110 determines that the ECAP characteristic values are increasing or decreasing in an exponential or logarithmic manner, or the characteristic values oscillate during the sweep, IMD 110 may determine that patient transient movement may be the cause of the unexpected ECAP characteristic values.

In other examples, IMD 110 may detect the transient movement using other detected signals and/or sensors. In one example, IMD 110 may receive an electromyogram (EMG) signal from electrodes of leads 130, or some other electrodes of a connected lead or from a separate device, during the sweep. IMD 110 may analyze the EMG signal and determine that patient 105 has engaged in transient movement during the sweep. In other examples, IMD 110 may receive information from other sensors during the sweep that may indicate transient movement. For example, a sensor may include one or more accelerometers (or other movement detecting devices), and processing circuitry of IMD 110 may receive information from the sensor and determine that patient 105 has engaged in transient movement based on the movement detected by the one or more accelerometers. In some examples, IMD 110 may monitor information from two or more sensors, and/or using two or more sensing modalities, and determine that a transient movement occurred during a sweep based on this information from these two or more sensors and/or two or more modalities. IMD 110 may determine a transient movement if any one of the sensors and/or sensing modalities indicate that a transient movement occurred. Alternatively, IMD 110 may require that information from at least two or more sensors and/or sensing modalities agree that a transient movement has occurred.

IMD 110 may also determine the calibration growth curve for each of a plurality of posture states. For example, IMD 110 may be configured to, for each posture state of the plurality of posture states, control the stimulation circuitry to deliver a plurality of calibration electrical stimulation pulses having different amplitude values while the patient assumes the posture state and control the sensing circuitry to detect, after delivery of each calibration electrical stimulation pulse of the plurality of calibration electrical stimulation pulses, a respective calibration ECAP signal of a plurality of calibration ECAP signals. IMD 110 may then determine calibration characteristic values for the plurality of calibration ECAP signals, where each calibration ECAP signal of the plurality of calibration ECAP signals are associated with a respective characteristic value of the calibration characteristic values. IMD 110 may then determine a respective calibration growth curve, of the plurality of calibration growth curves, that represents the relationship between the calibration characteristic values of the plurality of calibration ECAP signals and the different amplitude values of the plurality of calibration electrical stimulation pulses from which the calibration ECAP signals were evoked. IMD 110 may perform this process again at any time, as a scheduled task or in response to a trigger. For example, IMD 110 may recalibrate these calibration growth curves in response to receiving information indicative of ineffective therapy, a user request to recalibrate the growth curves, and/or determining that a predetermined time has elapsed.

As described herein, IMD 110 may then compare a growth curve determined during posture state sensing to the most current calibration growth curves for the posture states. IMD 110 may select the posture state associated with the calibrated growth curve closest to the determined growth curve. The comparison may include comparing the slope of the growth curves and/or the offset of the growth curves (e.g., the magnitude of the y-intercept of the growth curve). In some examples, IMD 110 may employ an acceptable deviation for the growth curve when compared to the calibration growth curves before IMD 110 will positively identify the posture state. This mechanism may prevent IMD 110 from identifying a posture state when the determined growth curve does not appropriately match any calibrated growth curve in memory. If the determined growth curve is outside of the acceptable deviation, IMD 110 may responsively perform another sweep for ECAP signals in order to generate a new growth curve. In other examples, IMD 110 may determine the posture state from another sensor, such as an accelerometer. In some examples in which IMD 110 cannot positively determine the posture state of the patient, IMD 110 may revert to a "safe mode" in which stimulation parameter value adjustment is performed based on a conservative parameter value adjustment scheme or disable parameter value adjustment based on posture state detection.

Although in one example IMD 110 takes the form of an SCS device, in other examples, IMD 110 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine stimulation thresholds (e.g., perception thresholds and detection thresholds) associated any one of the aforementioned IMDs and then use a stimulation threshold to inform the intensity (e.g., stimulation levels) of therapy.

Figure 2:
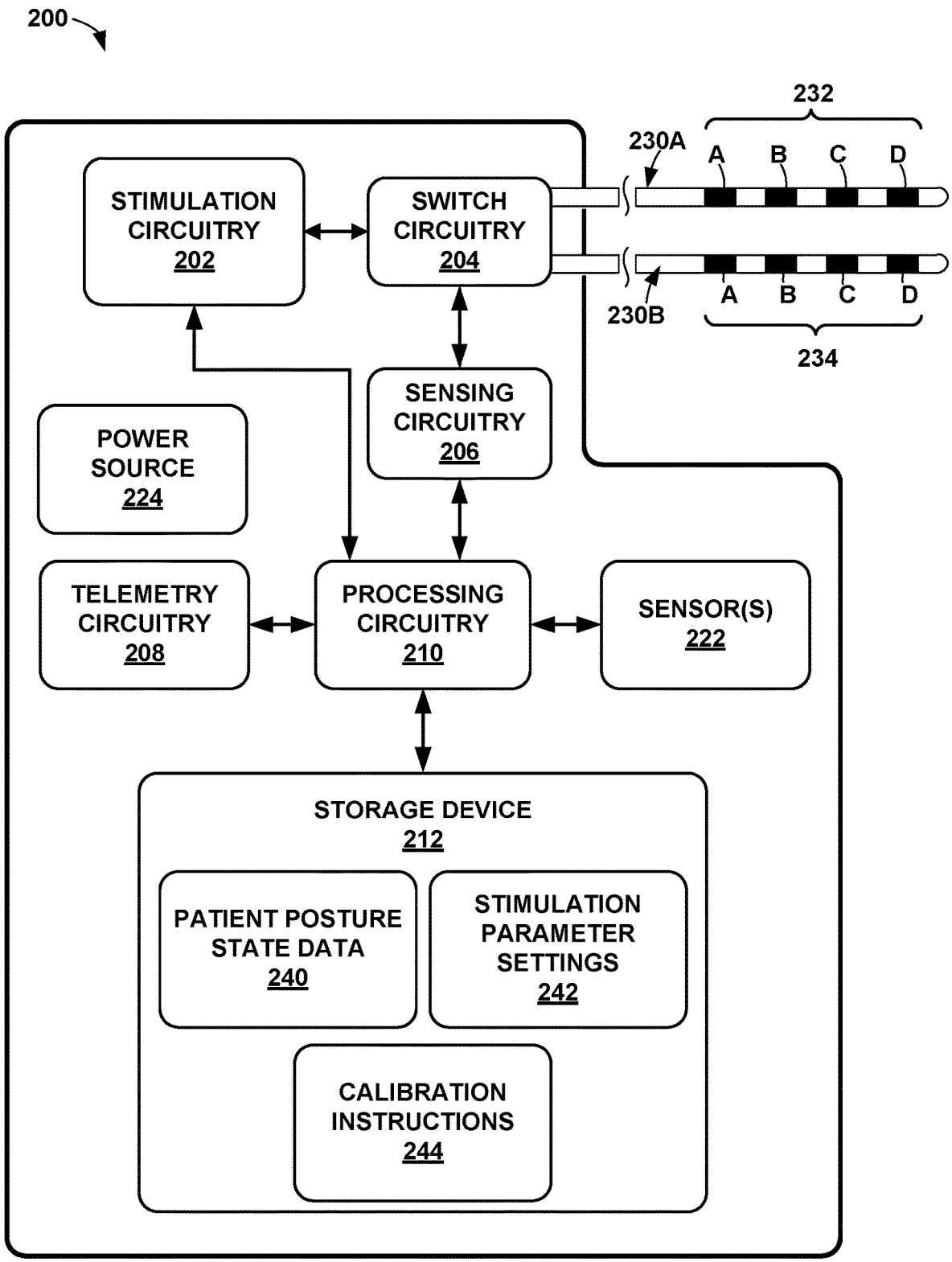
FIG. 2 is a block diagram illustrating an example configuration of components of an implantable medical device (IMD), in accordance with one or more techniques of this disclosure.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, and power source 224.

In the example shown in FIG. 2, storage device 212 stores patient posture state data 240, stimulation parameter settings 242, and calibration instructions 244 in separate memories within storage device 212 or separate areas within storage device 212. In some examples, stimulation parameter settings 242 may include stimulation parameter values for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, and pulse shape. Storage device 212 may also store ECAP test stimulation programs, as part of stimulation parameter settings 242 or as a separate memory area, that defines values for a set of electrical stimulation parameters (e.g., a control stimulation parameter set) configured to elicit a detectable ECAP signal, such as a stimulation electrode combination, electrode polarity, current or voltage amplitude, pulse width, pulse rate, and pulse shape. ECAP test stimulation programs may also have additional information such as instructions regarding when to deliver control pulses based on the pulse width and/or frequency of the informed pulses defined in stimulation parameter settings 242.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 is configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP signals. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IM 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs. For instance, electrodes 232 and 234 may sense the voltage amplitude of a portion of the ECAP signals, where the sensed voltage amplitude, such as the voltage difference between features within the signal, is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store patient posture state data 240, stimulation parameter settings 242, and calibration instructions 244.

Patient posture state data 240 may store growth curves or other ECAP related data and indications of one or more posture states to which the growth curves or other ECAP related data is associated. For example, each posture state may be associated with a respective a growth curve of ECAP characteristic values. In some examples, multiple posture states may be associated with the same growth curve. In this manner, processing circuitry 210 may compare a newly determined growth curve (determined from a plurality of ECAP signals) to the growth curves stored in patient posture state data 240 to determine the current posture state of the patient for the time at which the ECAP signals were detected.

Calibration instructions 244 may include instructions for how to determine calibrated growth curves for each posture state and/or when to recalibrate the calibrated grown curves. For example, calibration instructions 244 may define the parameter values of the pulses used to elicit ECAP signals, how many pulses and ECAP signals should be used to define each growth curve, the type of ECAP characteristic value to use when defining the growth curve, or any other similar information.

In some examples, storage device 212 may also store instructions on how processing circuitry 210 can adjust stimulation pulses in response to the detected posture state. For example, processing circuitry 210 may select a specific program, or set of stimulation parameter values, associated with a particular posture. In other examples, processing circuitry 210 may select a gain value or other factor that defines determines how a stimulation parameter value may be changed based on a detected ECAP characteristic value. Processing circuitry 210 may monitor ECAP characteristic values obtained from ECAP signals to modulate stimulation parameter values (e.g., increase or decrease stimulation intensity to maintain a target therapeutic effect). Since a target ECAP characteristic value may vary for different posture states, processing circuitry 210 may select the appropriate target ECAP characteristic value for the current posture state of the patient and modulate stimulation parameter values based on that posture state-specific target ECAP characteristic value.

Sensor(s) 222 may include one or more sensing elements that sense values of a respective patient parameter, such as posture state. As described, electrodes 232 and 234 may be the electrodes that sense the characteristic value of the ECAP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity, and processing circuitry 210 may increase the frequency of control pulses and ECAP sensing in response to detecting increased patient activity. In one example, processing circuitry 210 may initiate control pulses and corresponding ECAP sensing in response to a signal from sensor(s) 222 indicating that patient activity has exceeded an activity threshold. In some examples, processing circuitry 210 may initiate a new sweep for ECAP signals to determine a growth curve in response to detecting the exceeded activity threshold. Conversely, processing circuitry 210 may decrease the frequency of control pulses and ECAP sensing (e.g., the frequency of sweeps) in response to detecting decreased patient activity. For example, in response to sensor(s) 222 no longer indicating that the sensed patient activity exceeds a threshold, processing circuitry 210 may suspend or stop delivery of control pulses and ECAP sensing. In this manner, processing circuitry 210 may dynamically deliver control pulses and sense ECAP signals based on patient activity to reduce power consumption of the system when the electrode-to-neuron distance is not likely to change and increase system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to patient 105). In some examples, signals from sensor(s) 222 indicate a position or body state (e.g., sleeping, awake, sitting, standing, or the like), and processing circuitry 210 may select target ECAP characteristic values according to the indicated position or body state.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
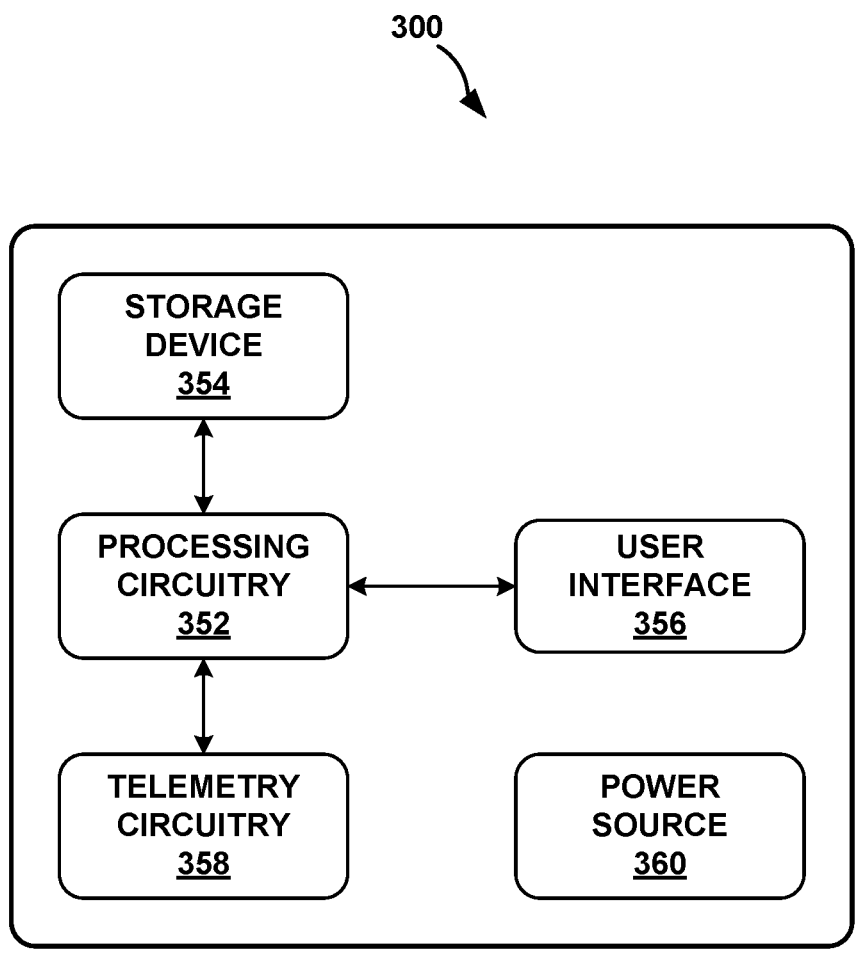
FIG. 3 is a block diagram illustrating an example configuration of components of an example external programmer, in accordance with one or more techniques of this disclosure.

FIG. 3 is a block diagram illustrating an example configuration of components of an example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode pattern, or receive a user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified posture states, sensed patient parameter values, or any other such information. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode pattern or a change to an existing spatial electrode pattern, of the input may request some other change to the delivery of electrical stimulation. During the calibration process of obtaining ECAP signals for different posture states, user interface 356 may present the posture state that the patient should assume, and user interface 356 may receive user input confirming that the patient is in the requested posture state. In other examples, user interface 356 may receive user input indicating the posture state that the patient is in and generate the relationship of the detected ECAP characteristic values obtained during the calibration (e.g., the calibrated growth curve) for that indicated posture state.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

User interface 356 of external programmer 300 may also be configured to receive an indication from a clinician instructing a processor of the medical device to update one or more therapy stimulation programs or to update the calibrated growth curves for one or more posture states. Updating therapy stimulation programs and calibrated growth curves may include changing one or more parameters of the stimulation pulses delivered by the medical device according to the programs, such as amplitude, pulse width, frequency, and pulse shape of the informed pulses and/or control pulses. User interface 356 may also receive instructions from the clinician commanding any electrical stimulation, including therapy stimulation and control stimulation to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
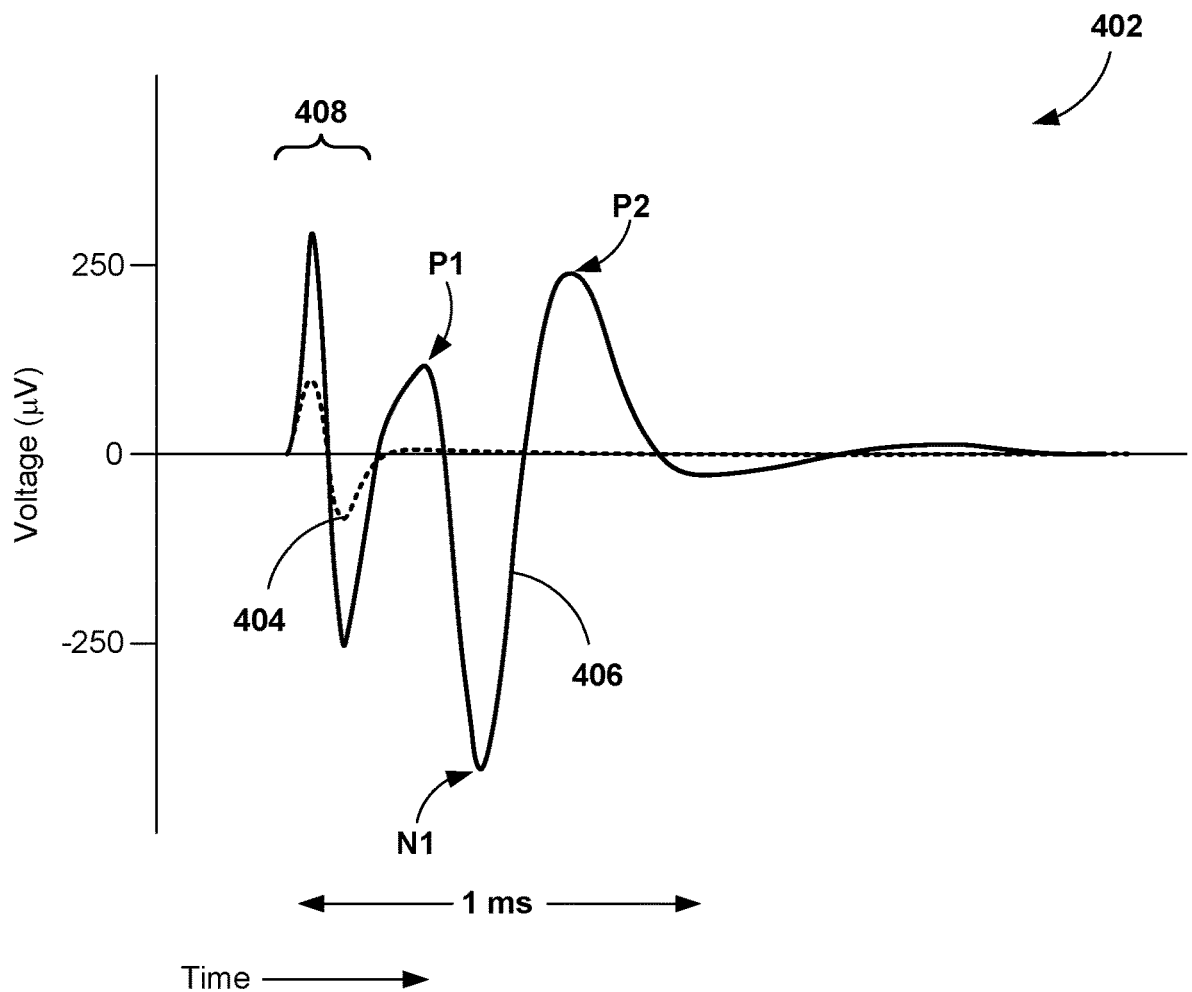
FIG. 4 is a graph of example evoked compound action potentials (ECAPs) sensed for respective stimulation pulses, in accordance with one or more techniques of this disclosure.

FIG. 4 is a graph 402 of example evoked compound action potentials (ECAPs) sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from control pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse. In other words, the stimulation pulse did not elicit a detectable ECAP signal in ECAP signal 404. Peaks 408 of ECAP signal 404 are detected and represent the artifact of the delivered stimulation pulse (e.g., a control pulse that may or may not contribute to a therapeutic effect for the patient). However, no propagating signal is detected after the artifact in ECAP signal 404 because the control pulse was sub-detection threshold.

In contrast to ECAP signal 404, ECAP signal 406 represents the voltage amplitude detected from a supra-detection threshold control pulse. Peaks 408 of ECAP signal 406 are detected and represent the artifact of the delivered control pulse. After peaks 408, ECAP signal 406 also includes peaks P1, N1, and P2, which are three typical peaks representative of propagating action potentials from an ECAP. The example duration of the artifact and peaks P1, N1, and P2 is approximately 1 millisecond (ms). When detecting the ECAP of ECAP signal 406, different characteristics may be identified. For example, the characteristic of the ECAP may be the amplitude between N1 and P2. This N1-P2 amplitude may be easily detectable even if the artifact impinges on P1, a relatively large signal, and the N1-P2 amplitude may be minimally affected by electronic drift in the signal. In other examples, the characteristic of the ECAP used to detect the posture state of the patient and/or control informed pulses may be an amplitude of P1, N1, or P2 with respect to neutral or zero voltage. In some examples, the characteristic of the ECAP may be a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two points in the ECAP signal, such as the slope between N1 and P2. In other examples, the characteristic of the ECAP may be the time between two points of the ECAP, such as the time between N1 and P2. The time between two points in the ECAP signal may be referred to as a latency of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal generally increases with increased amplitude of the control pulse, as long as the pulse amplitude is greater than threshold such that nerves depolarize and propagate the signal. As discussed herein, the relationship between ECAP signal amplitude and pulse amplitude also depends on the posture state of the patient, so the relationship between the ECAP signal and pulse amplitude changes for different posture states. The target ECAP characteristic (e.g., the target ECAP amplitude) may be determined from the ECAP signal detected from a control pulse when informed pulses are determined to deliver effective therapy to patient 105. The ECAP signal thus is representative of the distance between the stimulation electrodes and the nerves appropriate for the stimulation parameter values of the informed pulses delivered at that time. IM 110 may attempt to use the detected posture state from an ECAP characteristic value and detected changes to the measured ECAP characteristic value to change informed pulse parameter values and maintain the target ECAP characteristic value during informed pulse delivery.

Figure 5:
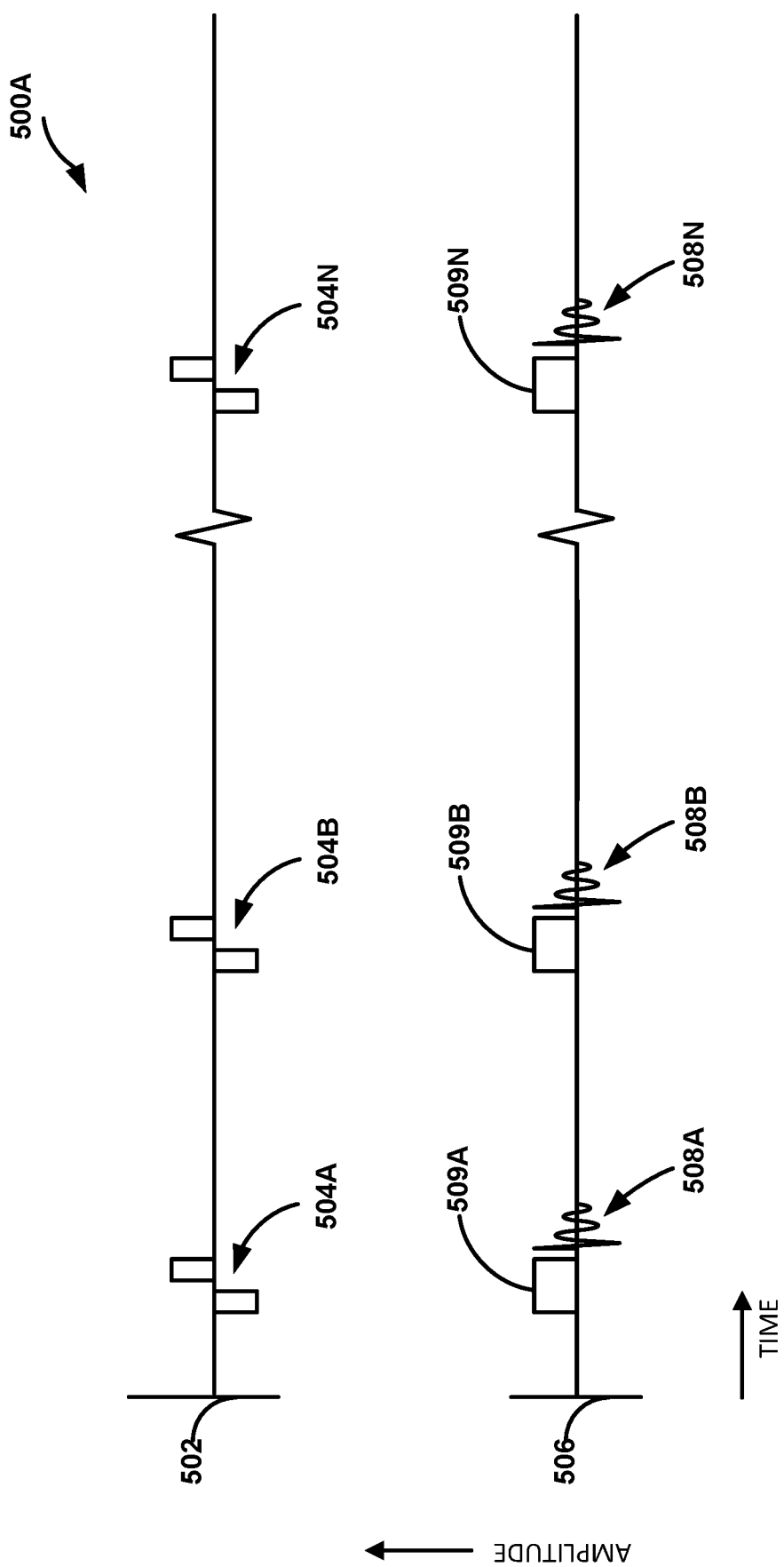
FIG. 5 is a timing diagram illustrating one example of electrical stimulation pulses and respective sensed ECAPs, in accordance with one or more techniques of this disclosure.

FIG. 5 is a timing diagram 500A illustrating one example of electrical stimulation pulses and respective sensed ECAPs, in accordance with one or more techniques of this disclosure. For convenience, FIG. 5 is described with reference to IMD 200 of FIG. 2. As illustrated, timing diagram 500A includes first channel 502, a plurality of control pulses 504A-504N (collectively "control pulses 504"), second channel 506, a plurality of respective ECAPs 508A-508N (collectively "ECAPs 508"), and a plurality of stimulation interference signals 509A-509N (collectively "stimulation interference signals 509"). In the example of FIG. 5, control pulses 504 may be configured to contribute to therapy or not contribute to therapy. In any case, control pulses 504 may elicit respective ECAPs 508 for the purpose of determining a relationship between the parameter values of control pulses 504 and ECAPs 508, such as a growth curve that is indicate of the posture state of the patient.

First channel 502 is a time/voltage (and/or current) graph indicating the voltage (or current) of at least one electrode of electrodes 232, 234. In one example, the stimulation electrodes of first channel 502 may be located on the opposite side of the lead as the sensing electrodes of second channel 506. Control pulses 504 may be electrical pulses delivered to the spinal cord of the patient by at least one of electrodes 232, 234, and control pulses 504 may be balanced biphasic square pulses with an interphase interval. In other words, each of control pulses 504 are shown with a negative phase and a positive phase separated by an interphase interval. For example, a control pulse 504 may have a negative voltage for the same amount of time and amplitude that it has a positive voltage. It is noted that the negative voltage phase may be before or after the positive voltage phase. Control pulses 504 may be delivered according to instructions stored in storage device 212 of IMD 200.

In some examples, each of control pulses 504 may be a part of a sweep of pulses configured to determine a relationship between the stimulation parameter values of the pulses and a characteristic value of the resulting respective ECAPs 508. For example, the relationship may be a growth curve of ECAP voltage amplitude versus pulse current amplitude. In this manner, each of control pulses 504 may differ from each other by a parameter value, such as an iteratively increasing current amplitude. In one example, control pulses 504 may have a pulse width of less than approximately 300 microseconds (e.g., the total time of the positive phase, the negative phase, and the interphase interval is less than 300 microseconds). In another example, control pulses 504 may have a pulse width of approximately 100 □s for each phase of the bi-phasic pulse. In some examples, the pulse width of control pulses 504 may be longer than 300 microseconds, as long as the pulse width does not interfere with the detection of the desired one or more features of the elicited ECAPs 508. As illustrated in FIG. 5, control pulses 504 may be delivered via channel 502. Delivery of control pulses 504 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 506 is a time/voltage (and/or current) graph indicating the voltage (or current) of at least one electrode of electrodes 232, 234. In one example, the electrodes of second channel 506 may be located on the opposite side of the lead as the electrodes of first channel 502. ECAPs 508 may be sensed at electrodes 232, 234 from the spinal cord of the patient in response to control pulses 504. ECAPs 508 are electrical signals which may propagate along a nerve away from the origination of control pulses 504. In one example, ECAPs 508 are sensed by different electrodes than the electrodes used to deliver control pulses 504. As illustrated in FIG. 5, ECAPs 508 may be recorded on second channel 506.

Stimulation interference signals 509A, 509B, and 509N (e.g., the artifact of the stimulation pulses) may be sensed by leads 230 and may be sensed during the same period of time as the delivery of control pulses 504. Since the interference signals may have a greater amplitude and intensity than ECAPs 508, any ECAPs arriving at IMD 200 during the occurrence of stimulation interference signals 509 may not be adequately sensed by sensing circuitry 206 of IMD 200. However, ECAPs 508 may be sufficiently sensed by sensing circuitry 206 because each ECAP 508, or at least a portion of ECAP 508 that includes one or more desired features of ECAP 508 that is used to detect the posture state and/or as feedback for control pulses 504, falls after the completion of each a control pulse 504. As illustrated in FIG. 5, stimulation interference signals 509 and ECAPs 508 may be recorded on channel 506.

In some examples, IMD 200, for example, may deliver the entire group of control pulses 504 (e.g., a sweep) consecutively and without any other intervening pulses in order to detect ECAPs 508 from which respective characteristic values are determined. IM 200 may then determine the relationship between the characteristic values from ECAPs 508 and the different parameter values of control pulses 504. In one example, the sweep of pulses 504 may be delivered by IMD 200 during a break in delivery of therapy pulses. In other examples, the sweep of pulses 504 may be at least partially interleaved with different stimulation pulses configured to contribute to therapy of the patient (e.g., one or more informed pulses). One or more pulses may thus be configured to contribute to therapy may be delivered between at least two of control pulses 504.

FIG. 6 is a graph 600 illustrating example growth curves 604, 606, and 608 for a relationship between ECAP amplitude and pulse amplitude for different posture states. As shown in FIG. 6, graph 600 illustrates example ECAP characteristic values 602 shown as dots, squares, and triangles for respective different current amplitudes of stimulation pulses. Typically, ECAPs will not be detectable until the stimulation pulse amplitude reaches a certain threshold, approximately at 4.5 mA current in the example of FIG. 6. Then, as the current amplitude is increased, the ECAP amplitude also increases approximately linearly. This linear relationship is shown by each of growth curves 604, 606, and 608.

The slope of each growth curve that linearly increases may be referenced as the "gain" herein, as it indicates the relationship between sensed ECAP amplitudes (e.g., a characteristic value) and pulse amplitudes. Put another way, the gain value may represent the slope of the growth curve of values of the characteristic of ECAP signals (e.g., an amplitude such as the N1-P2 amplitude or the amplitude of any peak of the ECAP signal) elicited from respective calibration stimulation pulses delivered to the patient and at least partially defined by different values of a stimulation parameter (e.g., current amplitude, voltage amplitude, or pulse width). As described herein, the gain value or slope may be associated with a particular posture state of a plurality of posture states. In some examples, the gain value for a patient may be used to dynamically adjust informed pulse amplitude and control amplitude based on the sensed ECAP amplitudes.

Each of growth curves 604, 606, and 608 represent growth curves for respective posture states. For example, four characteristic values 602 (circles) from respective ECAP signals form growth curve 604 may be associated with a supine posture state. Four characteristic values 602 (squares) from respective ECAP signals form growth curve 606 may be associated with a sitting upright posture state. Four characteristic values 602 (triangles) from respective ECAP signals form growth curve 608 may be associated with a prone posture state. Growth curves 604, 606, and 608 may be examples of calibrated growth curves. Each of growth curves 604, 606, and 608 may have corresponding slopes, such as approximately 32 □V/mA for growth curve 604, approximately 24 □V/mA for growth curve 606, and approximately 10 □V/mA for growth curve 608. Therefore, if a later determined growth curve from a sweep of pulses and corresponding ECAP signals results in a slope of approximately 24 □V/mA, the IMD may determine that the patient's posture state is sitting upright. In this manner, the different growth curves manifest as a function of the posture state of the patient due to the different distance between the electrodes and target nerves at these different posture states.

IMD 200, for example, may generate calibration growth curves (e.g., a type of relationship between parameter values and ECAP characteristic values) after implantation and prior to delivery of therapy. IMD 200 may periodically regenerate the calibration growth curves over time. For example, IMD 200 may have instructions that indicate a time interval that, upon expiring, triggers IMD 20*o* to regenerate the calibration growth curves. This recalibration maybe useful over time because electrodes may migrate in tissue, nerves may become desensitized to stimulation and/or electrodes may be encapsulated by tissue which changes deliverable and detectable voltages to and from tissue. In some examples, IMD 200 may regenerate calibration growth curves in response to a trigger, such as frequent user adjustment to stimulation parameter values during therapy, identification of reduced therapy efficacy, and/or receiving a user request to recalibrate.

IMD 200 may also periodically perform sweeps of pulses at different parameter values in order to determine the current growth curve and associated current posture state of the patient. These periodic sweeps may be programmed to occur at predetermined intervals, such as an interval in the range from approximately 1 second to approximately 1 hour, from approximately 5 seconds to approximately 10 minutes, or from approximately 10 seconds to approximately 1 minute. In some examples, the interval may change based on activity of the patient. For example, IMD 200 may shorten the interval if different posture states are detected more frequently. Conversely, IMD 200 may lengthen the interval if the same posture state is detected over several consecutive sweeps. IMD 200 may also use different intervals during different times of the day. For example, IMD 200 may employ longer intervals between sweeps during times at which the patient historically is sleeping and shorter intervals between sweeps during times at which the patient is historically engaging in activity.

Figure 7:
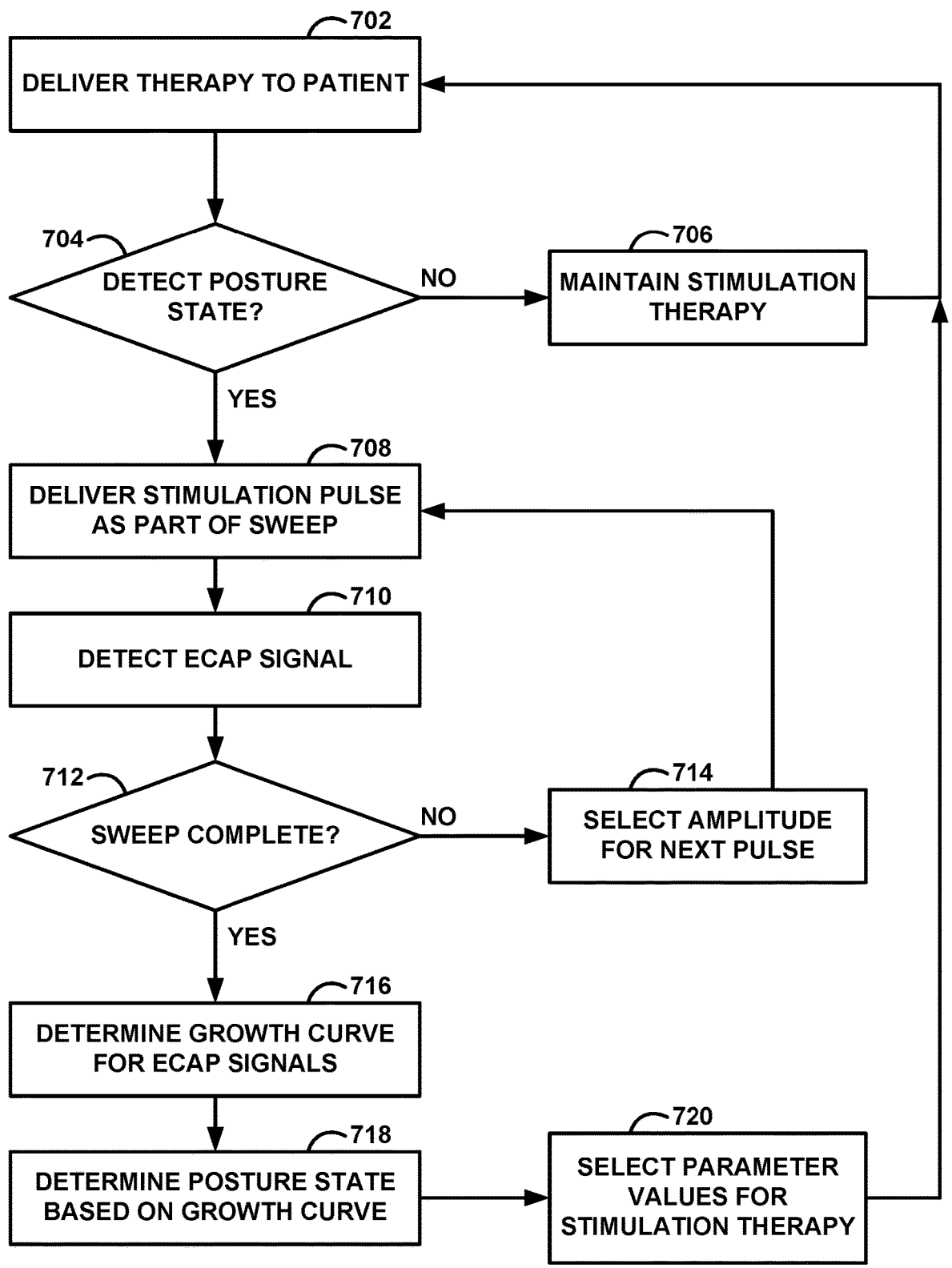
FIG. 7 is a flow diagram illustrating an example technique for determining a posture state for a patient and controlling therapy based on the posture state, in accordance with one or more techniques of this disclosure.

FIG. 7 is a flow diagram illustrating an example technique for determining a posture state for a patient and controlling therapy based on the posture state, in accordance with one or more techniques of this disclosure. For convenience, FIG. 7 is described with respect to IMD 200 of FIG. 2. However, the techniques of FIG. 7 may be performed by different components of IMD 200 or by additional or alternative medical devices. FIG. 7 will be described using control pulses for eliciting detectable ECAP signals, where the control pulses may be therapeutic or non-therapeutic to the patient. IMD 200, for example, may use detected ECAP signals to determine a posture state and then determine one or more parameters of the control pulses based on the posture state. IMD 200 may also, or alternatively, determine one or more parameters of a set of informed pulses, determine one or more parameters of other pulses that do not elicit ECAPs, or any combination thereof. Although processing circuitry 210 will be described as performing much of the technique of FIG. 7, other components of IMD 200 and/or other devices may perform some or all of the technique in other examples.

In the example operation of FIG. 7, processing circuitry 210 controls stimulation circuitry 202 to deliver therapy to a patient (702). The therapy may involve delivery of stimulation pulses configured to contribute to therapy for a patient. Processing circuitry 210 may then determine whether or not the posture state of the patient should be detected (704). If processing circuitry 210 does not have instructions to detect the posture state of the patient ("NO" branch of block 704), processing circuitry 210 may maintain stimulation therapy (706) and continue to deliver therapy to the patient (702). If processing circuitry 210 does have instructions to detect the posture state of the patient ("YES" branch of block 704), processing circuitry 210 controls stimulation circuitry 202 to deliver the first stimulation pulse (e.g., a control pulse) as part of a sweep of pulses with different parameter values (708). Processing circuitry 210 controls sensing circuitry 206 to detect the ECAP signal elicited by the stimulation pulse (710). If there are more stimulation pulses of the sweep to be delivered ("YES" branch of block 712), processing circuitry 210 selects the next stimulation parameter value (e.g., the next amplitude) for the next stimulation pulse of the sweep (714) and controls stimulation circuitry 202 to deliver the next stimulation pulse of the sweep (708). A sweep of stimulation pulses may include at least two pulses, four or more pulses, or six or more pulses. Although more pulses may enable a more accurate relationship, as few pulses as possible may be used to reduce the amount of time needed to deliver pulses of the sweep and sense the resulting ECAP signals.

If there are no more stimulation pulses of the sweep to be delivered ("NO" branch of block 712), processing circuitry 210 analyzes the detected ECAP signals from the sweep and determines the growth curve for these detected ECAP signals (716). The analysis of the detected ECAP signals may include determining at least one characteristic value for each ECAP signal (e.g., an amplitude between the N1-P2 peaks, area under the N1 and/or P2 peaks, or other measure) and then associating that characteristic value to at least one parameter value (e.g., pulse current amplitude) that defined the stimulation pulse that elicited the characteristic value. All of the characteristic values and associated parameter values an be plotted, and processing circuitry 210 may determine a best fit line to the points and determine the slope of that best fit line. In other examples, processing circuitry 210 may determine a relationship between the ECAP characteristic values and respective parameter values that is different than a growth curve.

Processing circuitry 210 may then determine the current posture state of the patient based on the determined growth curve (718). For example, processing circuitry 210 may compare the determined growth curve to a plurality of stored calibration growth curves and select the closest matching calibration growth curve. Processing circuitry 210 may select the posture state that is associated with the closest matching calibration growth curve. Processing circuitry 210 then selects one or more parameter values that define stimulation pulses of stimulation therapy to be delivered to the patient (702). For example, processing circuitry 210 may select parameter values, or a set of parameter values or therapy program, from memory that is stored for the selected posture state. Processing circuitry 210 then controls stimulation circuitry 202 to deliver therapy according to the newly selected parameter values (702).

In other examples, processing circuitry 210 may modulate stimulation therapy in a different manner using the determined posture state for the patient. For example, the posture state may be associated with a respective target ECAP characteristic value employed by processing circuitry 210 to adjust one or more stimulation parameter values. Processing circuitry 210 may periodically sense ECAP signals during the delivery of pulses configured to contribute to a therapeutic effect for the patient. The ECAP signals may be elicited by the pulses configured to provide the therapeutic effect (e.g., informed pulses) or pulses configured to elicit a detectable ECAP signal which may or may not contribute to a therapeutic effect (e.g., control pulses). In either case, if the characteristic value of the detected ECAP signal is greater than the target ECAP characteristic value for that posture state (or above an upper-bound of a threshold window associated with the target ECAP characteristic value), processing circuitry 210 may decrease the amplitude (or some parameter value affecting the pulse intensity) of the next stimulation pulses. If the characteristic value of the detected ECAP signal is less than the target ECAP characteristic value for that posture state (or below a lower-bound of a threshold window associated with the target ECAP characteristic value), processing circuitry 210 may increase the amplitude (or some parameter value affecting the pulse intensity) of the next stimulation pulses. Such a technique for modulating parameter values is described in the example of FIG. 8.

Figure 8:
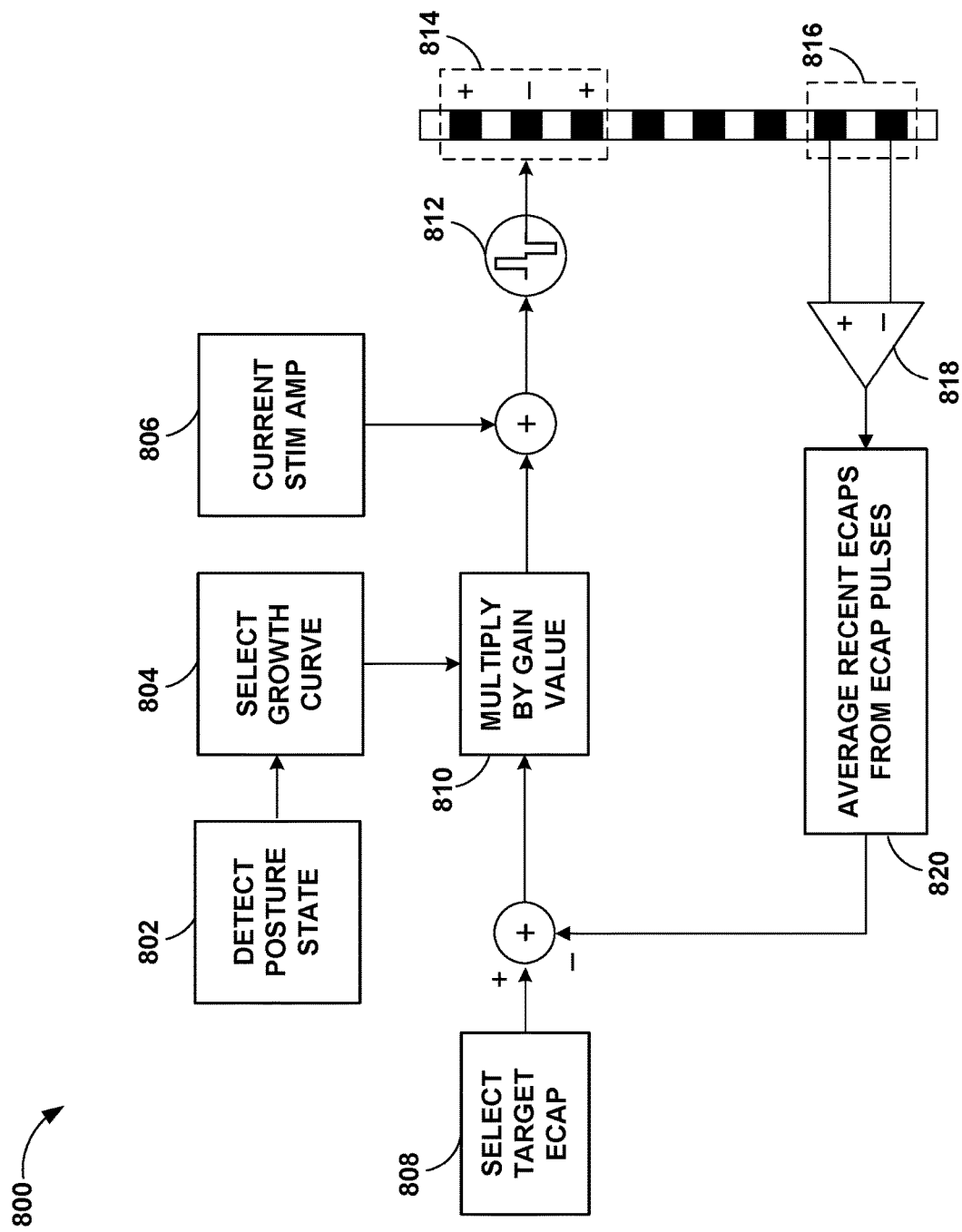
FIG. 8 is a diagram illustrating an example technique for adjusting stimulation therapy.

FIG. 8 is a diagram illustrating an example technique for adjusting stimulation therapy. As shown in the example of FIG. 8, the system, such as IMD 200 or any other device or system described herein, may dynamically adjust a parameter value that defines stimulation pulses based on a gain value representing the patient sensitivity to stimulation. Since the patient sensitivity to stimulation is dependent on posture state, IMD 200 may use the detected posture state from ECAP signals in order to tailor the gain value to the sensitivity of the patient at any given time. Processing circuitry 214 of IMD 200 may control stimulation circuitry 202 to deliver a stimulation pulse to a patient (e.g., a control pulse from which ECAP signals can be detected and may contribute to a therapeutic effect). Processing circuitry 202 may then control sensing circuitry 206 to sense an ECAP signal elicited by the control pulse and then identify a characteristic value of the ECAP signal (e.g., an amplitude of the ECAP signal). Processing circuitry 210 may then determine, based on the characteristic of the ECAP signal and a gain value (e.g., selected according to the detected posture state), a parameter value (e.g., an amplitude, pulse width value, pulse frequency value, and/or slew rate value) that at least partially defines another control pulse and/or an informed pulse (not shown). Processing circuitry 210 may then control stimulation circuitry 202 to deliver the next control pulse according to the determined parameter values.

As shown in FIG. 8, a control pulse 812 is delivered to the patient via electrode combination 814, shown as a guarded cathode of three electrodes. Control pulse 812 may be configured to contribute to a therapeutic effect for the patient. The resulting ECAP signal is sensed by the two electrodes at the opposing end of the lead of electrode combination 816 fed to a differential amplifier 818. For each sensed ECAP signal, processing circuitry 210 may measure an amplitude of a portion of the ECAP signal, such as the N1-P2 voltage amplitude from the portion of the ECAP signal. This amplitude of the ECAP signal may be the characteristic value for that ECAP signal. Processing circuitry 210 may average the recently measured ECAP amplitudes 820, such as averaging the most recent, and consecutive, 2, 3, 5, 5, 6, or more ECAP amplitudes. In some examples, the average may be a mean or median value. In some examples, one or more ECAP amplitudes may be ignored from the calculations if the amplitude value is determined to be an error. The measured amplitude (or average measured amplitude) is then subtracted from the selected target ECAP amplitude 808 to generate a differential amplitude. The selected target ECAP amplitude 808 may be determined from an ECAP sensed when the physician or patient initially discovers effective therapy from the informed pulses. This target ECAP amplitude 808 may essentially represent a reference distance between the stimulation electrodes and the target neurons (e.g., the spinal cord for the case of SCS). In some examples, processing circuitry 210 may select the target ECAP amplitude 808 associated with the detected posture state 802, to the extent the target ECAP amplitude would change for different posture states.

The differential amplitude is then multiplied by the gain value for the patient to generate a preliminary differential value 810. The preliminary differential value is added to the ECAP pulse amplitude 806 (e.g., the control pulse amplitude) to generate the new, or adjusted, ECAP pulse amplitude that at least partially defines the next control pulse 812.

Processing circuitry 210 may determine the gain value according to the detected posture state. As discussed herein, processing circuitry 210 may detect the current posture state 802 by determining a relationship between ECAP characteristic values and parameter values of pulses that elicited those ECAP characteristic values (e.g., during a sweep of pulses with different parameter values). For example, processing circuitry 210 may compare a determined growth curve to calibrated growth curves and select a posture state associated with the calibrated growth curve that most closely fits the determined growth curve. Processing circuitry 210 may then select the calibrated growth curve 804 from the selected posture state and employ the slope of that calibrated growth curve 804 as the gain value for the multiplication of step 810. In other examples, processing circuitry 210 directly use the slope of the determined growth curve as the gain value instead of, or in addition to, determining the posture state of the patient during which the ECAP signals were detected.

In some examples, processing circuitry 210 may adjust informed pulses, in addition to control pulses, when the informed pulses to not elicit detectable ECAP signals. For example, to adjust the informed pulse amplitude, the differential value that was created after multiplication by the gain value 810 is multiplied by a scaling factor to generate a therapy differential value. For example, the scaling factor may be the ratio of the previously delivered informed pulse amplitude to the previously delivered control pulse amplitude 806. The therapy differential value is then added to the previously delivered informed pulse amplitude to generate the new, or adjusted, informed pulse amplitude that at least partially defines the next informed pulse. This process can be applied to the informed pulses from multiple stimulation programs. For example, if informed pulses from two different stimulation programs are delivered as a part of stimulation therapy, the system may multiply the respective scaling factors by the differential value to obtain a respective therapy differential value for the informed pulses of each stimulation program. The next informed pulse (or pulses if multiple stimulation programs are involved in therapy) is then delivered, interleaved with the control pulse 812, to the patient via electrode combination 814 or a different set of electrodes in other examples. In some examples, at least two control pulses may be delivered, and at least two respective ECAP signals sensed, between consecutive informed pulses. This increased frequency of control pulses may allow the system to quickly adjust informed pulse amplitudes for any changes in the distance between electrodes and neurons.

Although the technique of FIG. 8 is described for adjusting the amplitude of the control pulses, other parameter values may be changed in other examples. For example, sensed ECAP signals may be used to increase or decrease the pulse width of the control pulse to adjust the amount of charge delivered to the tissue to maintain consistent volume of neural activation. In other examples, electrode combinations may be adjusted in order to deliver different amounts of charge and modify the number of neurons being recruited by each informed pulse. In other examples, processing circuitry 210 may be configured to adjust the slew rate of the control pulses (i.e., the rate of change of the voltage and/or amplitude at the beginning and/or end of the pulse or each phase of the pulse) in response to a characteristic of the ECAP signal, such as the amplitude of recent ECAP amplitudes.

The following examples are described herein. Example 1: a system comprising: stimulation circuitry configured to deliver electrical stimulation; sensing circuitry configured to sense a plurality of evoked compound action potential (ECAP) signals; and processing circuitry configured to: control the stimulation circuitry to deliver a plurality of electrical stimulation pulses having different amplitude values; control the sensing circuitry to detect, after delivery of each electrical stimulation pulse of the plurality of electrical stimulation pulses, a respective ECAP signal of the plurality of ECAP signals; and determine, based on the plurality of ECAP signals, a posture state of the patient.

Example 2: the system of example 1, wherein the processing circuitry is configured to: determine characteristic values for the plurality of ECAP signals, each ECAP signal of the plurality of ECAP signals being associated with a respective characteristic value of the characteristic values; determine a growth curve representing a relationship between the characteristic values of the plurality of ECAP signals and the different amplitude values of the plurality of electrical stimulation pulses from which the ECAP signals were evoked; compare the growth curve to a plurality of calibration growth curves associated with respective posture states of a plurality of posture states; and determine, based on the comparison, the posture state of the patient.

Example 3: the system of example 2, wherein the processing circuitry is configured to, for each posture state of the plurality of posture states: control the stimulation circuitry to deliver a plurality of calibration electrical stimulation pulses having different amplitude values while the patient assumes the posture state; control the sensing circuitry to detect, after delivery of each calibration electrical stimulation pulse of the plurality of calibration electrical stimulation pulses, a respective calibration ECAP signal of a plurality of calibration ECAP signals; determine calibration characteristic values for the plurality of calibration ECAP signals, each calibration ECAP signal of the plurality of calibration ECAP signals being associated with a respective characteristic value of the calibration characteristic values; and determine a respective calibration growth curve, of the plurality of calibration growth curves, that represents the relationship between the calibration characteristic values of the plurality of calibration ECAP signals and the different amplitude values of the plurality of calibration electrical stimulation pulses from which the calibration ECAP signals were evoked.

Example 4: the system of any of examples 1 through 3, wherein the processing circuitry is configured to control the stimulation circuitry to deliver the plurality of electrical stimulation pulses as a sweep of pulses comprising iteratively increasing amplitude values.

Example 5: the system of any of examples 1 through 4, wherein the plurality of electrical stimulation pulses is a second set of electrical stimulation pulses and the plurality of ECAP signals is a second set of ECAP signals, and wherein the processing circuitry is configured to: control, during a first period of time, the stimulation circuitry to deliver a first set of electrical stimulation pulses from which respective ECAP signals of a second set of ECAP signals can be detected; identify, during the first period of time, a transient movement of the patient; responsive to identifying the transient movement, terminate the first period of time and the delivery of the first set of electrical stimulation pulses and discard the second set of ECAP signals; determine that the transient movement has ended; and after the transient movement has ended, control the stimulation circuitry to deliver the second set of electrical stimulation pulses and control the sensing circuitry to detect the second set of ECAP signals.

Example 6: the system of example 5, wherein the processing circuitry is configured to, responsive to determining that the transient movement has ended, control the stimulation circuitry to deliver the second set of electrical stimulation pulses and control the sensing circuitry to detect the second set of ECAP signals.

Example 7: the system of any of examples 5 or 6, wherein the processor is configured to detect the transient movement from an electromyogram signal.

Example 8: the system of any of examples 5 through 7, wherein the processing circuitry is configured to detect the transient movement from information received from one or more accelerometers.

Example 9: the system of any of examples 1 through 8, wherein the posture state of the patient comprises at least one of a static posture of the patient or an activity level of the patient.

Example 10: the system of any of examples 1 through 9, the processing circuitry is configured to determine the posture state by selecting the posture state from a plurality of posture states, the plurality of posture states comprising at least two of a prone position, a supine position, a sitting position, and a standing position.

Example 11: the system of any of examples 1 through 10, wherein the different amplitude values are lower than a discomfort threshold for the patient.

Example 12: the system of any of examples 1 through 11, wherein the processing circuitry is configured to adjust, based on the determined posture state, a value of one or more parameters that at least partially define electrical stimulation therapy for the patient.

Example 13: the system of any of examples 1 through 12, wherein an implantable medical device comprises the stimulation circuitry, the sensing circuitry, and the processing circuitry.

Example 14: a method comprising: controlling, by processing circuitry, stimulation circuitry to deliver a plurality of electrical stimulation pulses having different amplitude values; controlling, by the processing circuitry, sensing circuitry to detect, after delivery of each electrical stimulation pulse of the plurality of electrical stimulation pulses, a respective evoked compound action potential (ECAP) signal of a plurality of ECAP signals; and determining, by the processing circuitry and based on the plurality of ECAP signals, a posture state of the patient.

Example 15: the method of example 14, further comprising: determining characteristic values for the plurality of ECAP signals, each ECAP signal of the plurality of ECAP signals being associated with a respective characteristic value of the characteristic values; determining a growth curve representing a relationship between the characteristic values of the plurality of ECAP signals and the different amplitude values of the plurality of electrical stimulation pulses from which the ECAP signals were evoked; comparing the growth curve to a plurality of calibration growth curves associated with respective posture states of a plurality of posture states; and determining, based on the comparison, the posture state of the patient.

Example 16: the method of example 15, further comprising, for each posture state of the plurality of posture states: controlling the stimulation circuitry to deliver a plurality of calibration electrical stimulation pulses having different amplitude values while the patient assumes the posture state; controlling the sensing circuitry to detect, after delivery of each calibration electrical stimulation pulse of the plurality of calibration electrical stimulation pulses, a respective calibration ECAP signal of a plurality of calibration ECAP signals; determining calibration characteristic values for the plurality of calibration ECAP signals, each calibration ECAP signal of the plurality of calibration ECAP signals being associated with a respective characteristic value of the calibration characteristic values; and determining a respective calibration growth curve, of the plurality of calibration growth curves, that represents the relationship between the calibration characteristic values of the plurality of calibration ECAP signals and the different amplitude values of the plurality of calibration electrical stimulation pulses from which the calibration ECAP signals were evoked.

Example 17: the method of any of examples 14 through 16, wherein controlling the stimulation circuitry to deliver the plurality of electrical stimulation pulses comprises controlling the stimulation circuitry to provide a sweep of pulses comprising iteratively increasing amplitude values.

Example 18: the method of any of examples 14 through 16, wherein the plurality of electrical stimulation pulses is a second set of electrical stimulation pulses and the plurality of ECAP signals is a second set of ECAP signals, and wherein the method further comprises: controlling, during a first period of time, the stimulation circuitry to deliver a first set of electrical stimulation pulses from which respective ECAP signals of a second set of ECAP signals can be detected; identifying, during the first period of time, a transient movement of the patient; responsive to identifying the transient movement, terminating the first period of time and the delivery of the first set of electrical stimulation pulses and discard the second set of ECAP signals; determining that the transient movement has ended; and after the transient movement has ended, controlling the stimulation circuitry to deliver the second set of electrical stimulation pulses and control the sensing circuitry to detect the second set of ECAP signals.

Example 19: the method of example 18, further comprising, responsive to determining that the transient movement has ended, controlling the stimulation circuitry to deliver the second set of electrical stimulation pulses and control the sensing circuitry to detect the second set of ECAP signals.

Example 20: the method of any of examples 18 and 19, further comprising detecting the transient movement from an electromyogram signal.

Example 21: the method of any of examples 18 through 20, further comprising detecting the transient movement from information received from one or more accelerometers.

Example 22: the method of any of examples 14 through 21, wherein the posture state of the patient comprises at least one of a static posture of the patient or an activity level of the patient.

Example 23: the method of any of examples 14 through 22, wherein determining the posture state comprises selecting the posture state from a plurality of posture states, the plurality of posture states comprising at least two of a prone position, a supine position, a sitting position, and a standing position.

Example 24: the method of any of examples 14 through 23, wherein the different amplitude values are lower than a discomfort threshold for the patient.

Example 25: the method of any of examples 14 through 24, further comprising adjusting, based on the determined posture state, a value of one or more parameters that at least partially define electrical stimulation therapy for the patient.

Example 26: a computer-readable medium comprising instructions that, when executed, causes processing circuitry to: control stimulation circuitry to deliver a plurality of electrical stimulation pulses having different amplitude values; control sensing circuitry to detect, after delivery of each electrical stimulation pulse of the plurality of electrical stimulation pulses, a respective evoked compound action potential (ECAP) signal of a plurality of ECAP signals; and determine, based on the plurality of ECAP signals, a posture state of the patient.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
   stimulation circuitry configured to deliver electrical stimulation;
   sensing circuitry configured to sense a plurality of evoked compound action potential (ECAP) signals; and
   processing circuitry configured to:
      control the stimulation circuitry to deliver a plurality of electrical stimulation pulses having different amplitude values;
      control the sensing circuitry to detect, after delivery of each electrical stimulation pulse of the plurality of electrical stimulation pulses, a respective ECAP signal of the plurality of ECAP signals; and
      determine, based on the plurality of ECAP signals, a posture state of the patient.

2. The system of claim 1, wherein the processing circuitry is configured to:
   determine characteristic values for the plurality of ECAP signals, each ECAP signal of the plurality of ECAP signals being associated with a respective characteristic value of the characteristic values;
   determine a growth curve representing a relationship between the characteristic values of the plurality of ECAP signals and the different amplitude values of the plurality of electrical stimulation pulses from which the ECAP signals were evoked;
   compare the growth curve to a plurality of calibration growth curves associated with respective posture states of a plurality of posture states; and
   determine, based on the comparison, the posture state of the patient.

3. The system of claim 2, wherein the processing circuitry is configured to, for each posture state of the plurality of posture states:
   control the stimulation circuitry to deliver a plurality of calibration electrical stimulation pulses having different amplitude values while the patient assumes the posture state;
   control the sensing circuitry to detect, after delivery of each calibration electrical stimulation pulse of the plurality of calibration electrical stimulation pulses, a respective calibration ECAP signal of a plurality of calibration ECAP signals;
   determine calibration characteristic values for the plurality of calibration ECAP signals, each calibration ECAP signal of the plurality of calibration ECAP signals being associated with a respective characteristic value of the calibration characteristic values; and
   determine a respective calibration growth curve, of the plurality of calibration growth curves, that represents the relationship between the calibration characteristic values of the plurality of calibration ECAP signals and the different amplitude values of the plurality of calibration electrical stimulation pulses from which the calibration ECAP signals were evoked.

4. The system of claim 1, wherein the processing circuitry is configured to control the stimulation circuitry to deliver the plurality of electrical stimulation pulses as a sweep of pulses comprising iteratively increasing amplitude values.

5. The system of claim 1, wherein the plurality of electrical stimulation pulses is a second set of electrical stimulation pulses and the plurality of ECAP signals is a second set of ECAP signals, and wherein the processing circuitry is configured to:
   control, during a first period of time, the stimulation circuitry to deliver a first set of electrical stimulation pulses from which respective ECAP signals of a second set of ECAP signals can be detected;
   identify, during the first period of time, a transient movement of the patient;
   responsive to identifying the transient movement, terminate the first period of time and the delivery of the first set of electrical stimulation pulses and discard the second set of ECAP signals;
   determine that the transient movement has ended; and
   after the transient movement has ended, control the stimulation circuitry to deliver the second set of electrical stimulation pulses and control the sensing circuitry to detect the second set of ECAP signals.

6. The system of claim 5, wherein the processing circuitry is configured to, responsive to determining that the transient movement has ended, control the stimulation circuitry to deliver the second set of electrical stimulation pulses and control the sensing circuitry to detect the second set of ECAP signals.

7. The system of claim 5, wherein the processor is configured to detect the transient movement from an electromyogram signal.

8. The system of claim 5, wherein the processing circuitry is configured to detect the transient movement from information received from one or more accelerometers.

9. The system of claim 1, wherein the posture state of the patient comprises at least one of a static posture of the patient or an activity level of the patient.

10. The system of claim 1, wherein the processing circuitry is configured to determine the posture state by selecting the posture state from a plurality of posture states, the plurality of posture states comprising at least two of a prone position, a supine position, a sitting position, and a standing position.

11. The system of claim 1, wherein the different amplitude values are lower than a discomfort threshold for the patient.

12. The system of claim 1, wherein the processing circuitry is configured to adjust, based on the determined posture state, a value of one or more parameters that at least partially define electrical stimulation therapy for the patient.

13. The system of claim 1, wherein an implantable medical device comprises the stimulation circuitry, the sensing circuitry, and the processing circuitry.

14. A method comprising:
controlling, by processing circuitry, stimulation circuitry to deliver a plurality of electrical stimulation pulses having different amplitude values;
controlling, by the processing circuitry, sensing circuitry to detect, after delivery of each electrical stimulation pulse of the plurality of electrical stimulation pulses, a respective evoked compound action potential (ECAP) signal of a plurality of ECAP signals; and
determining, by the processing circuitry and based on the plurality of ECAP signals, a posture state of the patient.

15. The method of claim 14, further comprising:
determining characteristic values for the plurality of ECAP signals, each ECAP signal of the plurality of ECAP signals being associated with a respective characteristic value of the characteristic values;
determining a growth curve representing a relationship between the characteristic values of the plurality of ECAP signals and the different amplitude values of the plurality of electrical stimulation pulses from which the ECAP signals were evoked;
comparing the growth curve to a plurality of calibration growth curves associated with respective posture states of a plurality of posture states; and
determining, based on the comparison, the posture state of the patient.

16. The method of claim 15, further comprising, for each posture state of the plurality of posture states:
controlling the stimulation circuitry to deliver a plurality of calibration electrical stimulation pulses having different amplitude values while the patient assumes the posture state;
controlling the sensing circuitry to detect, after delivery of each calibration electrical stimulation pulse of the plurality of calibration electrical stimulation pulses, a respective calibration ECAP signal of a plurality of calibration ECAP signals;
determining calibration characteristic values for the plurality of calibration ECAP signals, each calibration ECAP signal of the plurality of calibration ECAP signals being associated with a respective characteristic value of the calibration characteristic values; and
determining a respective calibration growth curve, of the plurality of calibration growth curves, that represents the relationship between the calibration characteristic values of the plurality of calibration ECAP signals and the different amplitude values of the plurality of calibration electrical stimulation pulses from which the calibration ECAP signals were evoked.

17. The method of claim 14, wherein controlling the stimulation circuitry to deliver the plurality of electrical stimulation pulses comprises controlling the stimulation circuitry to provide a sweep of pulses comprising iteratively increasing amplitude values.

18. The method of claim 14, wherein the plurality of electrical stimulation pulses is a second set of electrical stimulation pulses and the plurality of ECAP signals is a second set of ECAP signals, and wherein the method further comprises:
controlling, during a first period of time, the stimulation circuitry to deliver a first set of electrical stimulation pulses from which respective ECAP signals of a second set of ECAP signals can be detected;
identifying, during the first period of time, a transient movement of the patient;
responsive to identifying the transient movement, terminating the first period of time and the delivery of the first set of electrical stimulation pulses and discard the second set of ECAP signals;
determining that the transient movement has ended; and
after the transient movement has ended, controlling the stimulation circuitry to deliver the second set of electrical stimulation pulses and control the sensing circuitry to detect the second set of ECAP signals.

19. The method of claim 18, further comprising, responsive to determining that the transient movement has ended, controlling the stimulation circuitry to deliver the second set of electrical stimulation pulses and control the sensing circuitry to detect the second set of ECAP signals.

20. The method of claim 18, further comprising detecting the transient movement from an electromyogram signal.

21. The method of claim 18, further comprising detecting the transient movement from information received from one or more accelerometers.

22. The method of claim 14, wherein the posture state of the patient comprises at least one of a static posture of the patient or an activity level of the patient.

23. The method of claim 14, wherein determining the posture state comprises selecting the posture state from a plurality of posture states, the plurality of posture states comprising at least two of a prone position, a supine position, a sitting position, and a standing position.

24. The method of claim 14, wherein the different amplitude values are lower than a discomfort threshold for the patient.

25. The method of claim 14, further comprising adjusting, based on the determined posture state, a value of one or more parameters that at least partially define electrical stimulation therapy for the patient.

26. A non-transitory computer-readable medium comprising instructions that, when executed, causes processing circuitry to:
control stimulation circuitry to deliver a plurality of electrical stimulation pulses having different amplitude values;
control sensing circuitry to detect, after delivery of each electrical stimulation pulse of the plurality of electrical stimulation pulses, a respective evoked compound action potential (ECAP) signal of a plurality of ECAP signals; and determine, based on the plurality of ECAP signals, a posture state of the patient.

* * * * *